(12) United States Patent
Danvy et al.

(10) Patent No.: US 6,878,723 B1
(45) Date of Patent: Apr. 12, 2005

(54) LTA$_4$ HYDROLASE INHIBITORS

(75) Inventors: Denis Danvy, Yvetot (FR); Thierry Monteil, Saint Georges sur Fontaine (FR); Jean-Christophe Plaquevent, Notre-Dame de Bondeville (FR); Pierre Duhamel, Mont-Saint-Aignan (FR); Lucette Duhamel, Mont-Saint-Aignan (FR); Nadine Noel, Moernach (FR); Claude Gros, Paris (FR); Olivier Chamard, Aulnay Sous Bois (FR); Jean-Charles Schwartz, Paris (FR); Jeanne-Marie Lecomte, Paris (FR); Serge Piettre, Saint Martin L'Hortier (FR)

(73) Assignees: Institut National de la Sante et de la rescherche Medicale (INSERM), Paris (FR); Bioprojet, Paris (FR)

( * ) Notice: Subject to any disclaimer, the term of this patent is extended or adjusted under 35 U.S.C. 154(b) by 0 days.

(21) Appl. No.: 09/958,160

(22) PCT Filed: Apr. 6, 2000

(86) PCT No.: PCT/FR00/00876

§ 371 (c)(1),
(2), (4) Date: Jan. 8, 2002

(87) PCT Pub. No.: WO00/59864

PCT Pub. Date: Oct. 12, 2000

(30) Foreign Application Priority Data

Apr. 6, 1999 (FR) .............................. 99 04271

(51) Int. Cl.$^7$ ...................... A01N 43/40; A61K 31/445; A61K 31/44; C07C 229/00
(52) U.S. Cl. ...................... 514/317; 514/318; 514/326; 514/327; 514/333; 514/334; 514/335; 514/345; 514/571; 514/572; 546/186; 546/188; 546/191; 546/193; 546/208; 546/212; 546/214; 546/216; 546/229; 546/238; 549/60; 549/65; 549/66; 549/77; 549/497; 549/499; 560/45; 560/121; 560/123; 560/124; 560/126; 562/444; 562/452; 562/498; 562/500; 562/503; 562/505
(58) Field of Search ................................ 514/317, 318, 514/326, 327, 333, 334, 335, 345, 351, 445, 571, 572, 467, 468, 573; 546/186, 188, 191, 193, 208, 212, 214, 216, 229, 238, 187, 192, 207; 549/60, 65, 66, 77, 497, 499, 475; 560/45, 121, 123, 124, 126; 562/444, 452, 498, 500, 503, 505, 506, 507

(56) References Cited

U.S. PATENT DOCUMENTS

| 3,553,258 A | * | 1/1971 | Kaiser et al. ............... 260/519 |
| 4,341,767 A | * | 7/1982 | Nestor et al. ................ 514/15 |
| 5,362,899 A | * | 11/1994 | Campbell .................. 558/108 |

OTHER PUBLICATIONS

Organic Chemistry, 2$^{nd}$ Edition. McMurry. pp. 970–974. Brooks/Cole Publishing Co. (1988).*

Takamura et al, "Optically Active Amino Acids. XV. alpha–Alkyl–alpha–amino acids. 8. 2–amino–2–methyl–3–buteneoic acid" Chem. Pharm. Bull. vol. 15(11), pp. 1776–1784 (1967).*

Coulter et al, "Structural and Conformational Analogues of I–Methionine as Inhibitors of the Enzymatic Synthesis of S–Adenosyl Methionine" Molecular Pharmacology, vol. 10, pp. 305–314 (1974).*

Wilson and Gisvold's Textbook of Organic, Medicinal and Pharmaceutical Chemistry, 9th ed. J.B. Lippincott Co., 1991.*

Lipinski et al, "Experimental and computational approaches to estimate solubility and permeability in drug discovery and development settings" Adv. Drug Delivery Rev. vol. 23, pp. 3–25 (1997).*

Liao et al, "Novel and Known Constituents from Buddleja Species and Their Activity against Leukocyte Eicosanoid Generation" J. Nat. Prod. vol. 62, pp. 1241–1245 (1999).*

Cichewicz et al, "Dimerization of Resveratrol by the Grapevine Pathogen Botrytis cinerea" J. Nat. Prod. vol. 63, pp. 29–33 (2000).*

Botting, Regina M., "Mechanism of Action of Acetaminophen: Is There a Cyclooxenase 3?" Clinical Infectious Diseases, 31 Suppl. 5, pp. S202–S210 (Oct. 2000).*

Likhitwitayawuid et al, "Flavonoids and Stilbenoids with COX–1 and COX–2 Inhibitory Activity from Dracaena lourein" Planta Medica, vol. 68(9), pp. 841–843 (Sep. 2002).*

* cited by examiner

Primary Examiner—Richard L. Raymond
Assistant Examiner—Zachary C. Tucker
(74) Attorney, Agent, or Firm—Stites & Harbison PLLC; B. Aaron Schulman

(57) ABSTRACT

The invention concerns compounds inhibiting LTA$_4$ hydrolase of formula (I). The invention also concerns their therapeutic, in particular anti-inflammatory, applications.

30 Claims, No Drawings

LTA4 HYDROLASE INHIBITORS

The present invention relates to compounds as defined hereinafter, which constitute a class of medicaments having mainly an anti-inflammatory activity and/or acting by inhibiting $LTA_4$ (leukotriene $A_4$) hydrolase, an enzyme which is responsible for the biosynthesis of leukotriene $LTB_4$, a major proinflammatory mediator.

It also relates to such compounds useful in the form of prodrugs.

It also relates to methods for preparing these compounds.

$LTA_4$ hydrolase (EC 3.3.2.6.) is an enzyme which is in particular present in the neutrophils and whose sequence has been recently shown (Funck et al., P.N.A.S., 1987, 89: 6677) to be related to that of a zinc metallopeptidase, aminopeptidase M (Malfroy et al., B.B.R.C., 1989, 161: 236). In agreement with the suggestion by Malfroy et al., it has been recognized that $LTA_4$ hydrolase possesses a zinc atom which is essential for its catalytic activity, an aminopeptidase-type activity, and is sensitive to the action of certain metallopeptidase inhibitors (Heggstrom et al., B.B.R.C., 1990, 173: 431; Minami et al., B.B.R.C., 1990, 173: 620).

The inhibition of $LTA_4$ hydrolase is capable of preventing the formation of $LTB_4$, a mediator responsible for the adhesion of the neutrophils to the endothelial cells and for their chemotaxis. It appears to be involved in the etiology or the symptomatology of a variety of conditions and inflammatory states such as rheumatoid arthritis, chronic inflammations of the intestine, multiple sclerosis, gout and psoriasis. In these processes, $LTB_4$ is thought to act in synergy with other metabolites of arachidonic acid which are produced by 5-lipoxygenase or cyclooxygenases whose inhibition is well known to produce anti-inflammatory effects.

Some $LTA_4$ hydrolase inhibiting compounds have been described, in particular in patent applications WO 94/00420, WO 96/11192, WO 96/10999 and WO 96/27585, WO 96/41625, WO 98/40354, WO 98/40364, WO 98/40370, WO 98/09943 and WO 98/43954.

The objective of the present invention is to provide novel compounds capable of inhibiting $LTA_4$ hydrolase.

The objective of the present invention is also to provide compounds which can be used as medicaments.

To this end, the subject of the invention is the use of compounds of formula (I) as defined below as inhibitors of the activity of $LTA_4$ hydrolase, in particular as anti-inflammatory agents.

The subject of the invention is also the use of these compounds of formula (I) in the form of prodrugs.

These compounds correspond to the following formula (I):

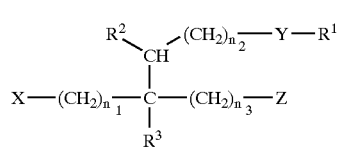

(I)

in which

X is selected from the following groups:

i)
—$NH_2$ ii)

$$-N{=}C\begin{array}{l}R^4\\R^5\end{array}$$

$n_1$ and $n_3$ are equal to 0 or 1, with $(n_1+n_3)$ equal to 0 or 1

$n_2$ varies from 0 to 10

Y is selected from the following groups:
  i) —O—
  ii) —$CH_2$—
  iii) —S—
  iv) —NH—
  v) —$OCH_2$—

$R^1$ is selected from the following groups:
  i) a hydrogen atom
  ii) a lower alkyl group
  iii) a cycloalkyl group
  iv) a phenyl group which is unsubstituted or which is mono- or polysubstituted with substituents selected from halogen atoms and $CF_3$, lower alkyl, lower alkoxy, $NH_2$, $NO_2$, CN, OH, $CO_2H$, OPh, $OCH_2Ph$, $SCH_3$, $SCH_2CH_3$ and $NHCOR^6$ groups
  v) an α- or β-naphthyl group
  vi) an anthracene group
  vii) —$A^2$—$(CH_2)_{n4}$—$A^1$ where $n_4$ varies from 0 to 4
     $A^1$ and $A^2$ are independently selected from the following groups:
     a) cycloalkyl
     b) phenyl which is unsubstituted or which is mono- or polysubstituted with substituents selected from halogen atoms and $CF_3$, lower alkyl and lower alkoxy groups,
     c) 2-, 3- or 4-pyridyl
     d) 2- or 3-thienyl
     e) 2- or 3-furyl
     f) 2-, 3- or 4-piperidyl
     g) cycloalkene
  viii) a 2-, 3- or 4-pyridyl group
  ix) a 2- or 3-thienyl group
  x) a 2- or 3-furyl group xi)

[structure with two fused rings and $n_5$ substituents]

Z is selected from the following groups:

i)
—$COOR^7$ ii)

$$-\underset{\underset{O}{\|}}{P}\begin{array}{l}OR^8\\OR^8\end{array}$$

iii)

[tetrazole ring with N—N, N—N, H]

iv)

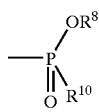

v) —SO$_3$H
vi) —SO$_2$NHR$^{11}$
vii) —CONHSO$_2$R$^{11}$

R$^2$ and R$^3$ are independently selected from the following groups:
i) a hydrogen atom
ii) a lower alkyl group
iii) a lower alkyl group substituted with a halogen atom
iv) a CF$_3$ group
v) a halogen atom R$^4$ and R$^5$ are independently selected from a hydrogen atom or a lower alkyl group, a phenyl group which is unsubstituted or which is substituted with a halogen atom, a CF$_3$ group, a lower alkyl group, a lower alkoxy group and an OH group.

n$_5$ varies from 0 to 2

R$^6$ represents a lower alkyl group

R$^7$ represents a hydrogen atom, a lower alkyl group, a group —(CH$_2$)$_{n6}$—Ph, n$_6$ varying from 0 to 4 and Ph being a phenyl group which is unsubstituted or which is mono- or polysubstituted with a halogen atom, a CF$_3$ group, a lower alkyl, a lower alkoxy or an OH group R$^8$ and R$^9$ are independently selected from a hydrogen atom, a phenyl group, a lower alkyl group and a lower acetylthioalkylene group R$^{10}$ represents a lower alkyl group, a group —(CH$_2$)$_{n7}$—Ph, n$_7$ varying from 1 to 6 and Ph being a phenyl group which is unsubstituted or which is mono- or polysubstituted with a halogen atom, a CF$_3$ group, a lower alkyl or a lower alkoxy R$^{11}$ represents a lower alkyl group or a phenyl group.

The expression lower alkyl group is understood to mean an alkyl group having a linear or branched chain containing from 1 to 10 carbon atoms, preferably 1 to 4 carbon atoms.

The expression lower alkoxy group is understood to mean an alkoxy group containing a linear or branched chain having from 1 to 10 carbon atoms, preferably 1 to 4 carbon atoms.

The expression cycloalkyl group is understood to mean a ring containing from 5 to 7 carbon atoms, preferably 6 carbon atoms, such as cyclopentane, cyclohexane or cycloheptane.

The expression cycloalkene group is understood to mean a ring containing from 5 to 7 carbon atoms and containing a double bond, preferably 6 carbon atoms, such as cyclohexene.

The expression lower acetylthioalkylene group is understood to mean an acetylthio group having a linear chain containing from 1 to 4 carbon atoms, preferably 1 to 2 carbon atoms.

The halogen atoms are preferably selected from chlorine and fluorine.

The invention also comprises the isomers of the compounds of formula (I), including the diastereoisomeric and enantiomeric forms.

The invention also extends to the therapeutically acceptable salts of these compounds, as well as to the salts of their isomers, including the diastereoisomeric and enantiomeric forms.

The expression therapeutically acceptable salts is understood to mean a salt which does not adversely affect either the chemical structure or the pharmacological properties of the compounds of the present invention. Such salts include inorganic and organic anions such as hydrochloride, hydrobromide, acetate, trifluoroacetate, maleate, fumarate, oxalate and the like, which are well known in the art. These salts are prepared in a conventional manner by neutralizing the compounds of formula (I) with the desired acid.

The subject of the invention is also the compounds of formula (I) per se, with the exception:

(α) of the compounds in which Z is a group of the COOR$^7$ type and n$_1$=n$_3$=0 and R$^2$=H and R$^1$ is a group iv) of the phenyl type which is unsubstituted or which is mono- or polysubstituted, and in which n$_2$=1, and (β) of the following compounds: α-amino-β-phenoxypropionic acid, 3-amino-7-phenylheptanoic acid, 3-amino-6-phenoxyhexanoic acid, α-amino-6-phenylhexanoic acid and α-amino-5-phenoxypentanoic acid.

The subject of the invention is also pharmaceutical compositions comprising at least one such compound.

The inventors have demonstrated that the compounds of formula (I) defined above, or their salts obtained with therapeutically acceptable inorganic or organic acids or their stereoisomers, possess a potent LTA$_4$ hydrolase inhibiting activity.

The compounds (I) exhibit, moreover, good bioavailability and have proved to have low toxicity.

The present invention describes a series of compounds capable of potently inhibiting LTA$_4$ hydrolase.

These compounds exhibit, in addition, biological activity as indicated hereinafter which confers therapeutic interest on them.

According to a first aspect of the invention, a preferred group of compounds of the abovementioned formula (I) comprises those for which X represents NH$_2$ and/or Z represents the group —COOR$^7$ with R$^7$ representing a hydrogen atom.

In this group, the compounds of formula (I) in which X is NH$_2$ and Z is COOH, are more particularly preferred.

The compounds of formula (I) in which R$^2$ and/or R$^3$ represent a hydrogen atom also constitute a particularly preferred subgroup according to the invention.

R$^2$ and R$^3$ are preferably each a hydrogen atom.

The compounds of formula (I) with R$^2$ and/or R$^3$ different from hydrogen represent another subgroup according to the invention.

A subfamily among the abovementioned compounds is formed by the compounds for which n$_1$ and n$_3$ are equal to 0.

Another subfamily consists of the compounds for which n$_1$ or n$_3$ is different from 0.

A subclass of compounds according to the invention also consists of those for which n$_2$=0. Among these compounds, Y preferably represents —O—.

Another subclass is formed by the compounds for which n$_2$ varies from 1 to 5, preferably from 2 to 5 and in a more particularly preferred manner for the compounds where n$_2$=3.

Another class of compounds according to the invention is defined by those where n$_2$ is greater than 5.

From the point of view of the symbol Y, the compounds for which the latter represents an oxygen atom are particularly preferred according to the invention.

Other subfamilies may be defined according to whether Y represents —CH$_2$—, a sulfur atom, a unit —NH— or —OCH$_2$—.

$R^1$ is preferably selected from a phenyl group which is unsubstituted or which is substituted, more preferably monosubstituted, with one of the abovementioned substituents.

When $R^1$ symbolizes a substituted phenyl group, the substituent(s) are preferably selected from lower alkyl, lower alkoxy, OPh and $OCH_2Ph$ groups.

The compounds for which $R^1$ is a phenyl group which is mono- or polysubstituted with an OPh group constitute a preferred subfamily according to the invention.

When $R^1$ represents a unit $-A^2-(CH_2)_{n4}-A^1$, $A^2$ is more preferably a phenyl group which is preferably unsubstituted.

Among these compounds, $n_4$ is preferably equal to 0 or 1 and $A^1$ is preferably selected from a phenyl, cycloalkyl and cycloalkene group.

$R^1$ representing a unit $-A^2-(CH_2)_{n4}-A^1$ is preferably a phenyl group substituted with a Ph, $CH_2Ph$, $CH_2$-cycloalkyl or $CH_2$-cycloalkene group, more preferably a $CH_2Ph$ or $CH_2$-cycloalkyl group.

Another subfamily comprises the compounds (I) for which $R^1$ represents a hydrogen atom or a lower alkyl group.

Another subfamily comprises the compounds (I) for which $R^1$ is a cycloalkyl group.

The compounds (I) with $R^1$ representing an α- or β-naphthyl group, or an anthracene group also form another subfamily.

Another group of compounds according to the invention comprises the compounds (I) with $R^1$ representing a 2-, 3- or 4-pyridyl, 2- or 3-thienyl and 2- or 3-furyl group.

The compounds (I) with $R^1$ representing

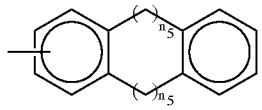

also form another subgroup according to the invention.

For all the subfamilies mentioned above, the substituents not specified may vary according to their respective general definitions.

A particularly preferred group of compounds according to the invention consists of the compounds corresponding to the following formula (II):

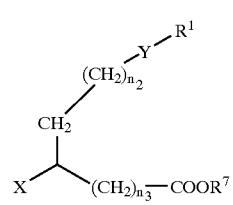

(II)

in which X, $n_2$, $n_3$, Y, $R^1$ and $R^7$ have the above meaning.

The preferences previously indicated for the compounds of formula (I) also apply to those of formula (II).

A group which is even more particularly preferred comprises the compounds corresponding to the following formula (III):

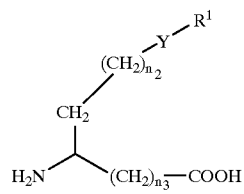

(III)

in which $n_2$, $n_3$, Y and $R^1$ have the meaning indicated above.

The particular choices mentioned for the compounds of formula (I) from the point of view of the symbols Y and $R^1$ also apply to the compounds of formula (III).

Among these compounds, those corresponding to the following formula (IV):

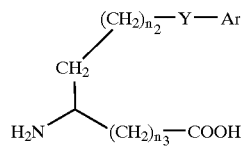

(IV)

where Y, $n_2$ and $n_3$ have the meaning given above and Ar symbolizes the group $R^1$ representing a phenyl group iv) optionally substituted as defined above or $R^1$ representing a group vii) $-A^2-(CH_2)_{n4}-A^1$, $A^2$ being a phenyl group (b) optionally substituted as defined above are particularly preferred.

According to a second aspect of the invention, a preferred group of compounds of formula (I) which is mentioned above comprises those for which X represents $NH_2$ and/or Z represents the group

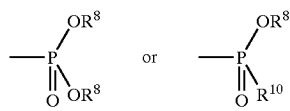

$R^8$, $R^9$ being a hydrogen atom, and $R^{10}$ having the abovementioned meaning.

In this group, the compounds of formula (I) in which X is $NH_2$ and Z is

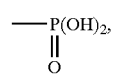

are more particularly preferred.

The compounds of formula (I) in which $R^2$ and/or $R^3$ represent a hydrogen atom also constitute a particularly preferred subgroup according to the invention.

$R^2$ and $R^3$ are preferably each a hydrogen atom.

The compounds of formula (I) with $R^2$ and/or $R^3$ different from hydrogen represent another subgroup according to the invention.

A subfamily among the abovementioned compounds is formed by the compounds for which $n_1$ and $n_3$ are equal to 0.

Another subfamily consists of the compounds for which $n_1$ and/or $n_3$ are different from 0.

A subclass of compounds according to the invention also consists of those for which $n_2$=0. Among these compounds, Y preferably represents —O—.

Another subclass is formed by the compounds for which $n_2$ varies from 1 to 5, preferably from 2 to 5 and in a more particularly preferred manner for the compounds where $n_2$=3.

Another class of compounds according to the invention is defined by those where $n_2$ is greater than 5.

From the point of view of the symbol Y, the compounds for which the latter represents an oxygen atom are particularly preferred according to the invention.

Other subfamilies may be defined according to whether Y represents —$CH_2$—, a sulfur atom, or a unit —NH— or —$OCH_2$—.

$R^1$ is preferably selected from a phenyl group which is unsubstituted or which is substituted, more preferably monosubstituted, with one of the abovementioned substituents.

When $R^1$ symbolizes a substituted phenyl group, the substituent(s) are preferably selected from halogen atoms, $CF_3$, lower alkyl, lower alkoxy, $NO_2$, CN, $NH_2$, $CO_2H$, OPh, $OCH_2Ph$ and $NHCOR^6$ groups.

The compounds for which $R^1$ is a phenyl group which is mono- or polysubstituted with halogen atoms or lower alkoxy groups constitute another subfamily according to the invention.

When $R^1$ represents a unit —$A^2$—$(CH_2)_{n4}$—$A^1$, $A^2$ is more preferably a phenyl group which is preferably unsubstituted.

Among these compounds, $n_4$ is preferably equal to 0 or 1 and $A^1$ is preferably a phenyl group.

$R^1$ representing a unit —$A^2$—$(CH_2)_{n4}$—$A^1$ is preferably a phenyl group substituted with a Ph or $CH_2Ph$ group, more preferably a $CH_2Ph$ group.

Another subfamily comprises the compounds (I) for which $R^1$ represents a hydrogen atom or a lower alkyl group.

Another subfamily comprises the compounds (I) for which $R^1$ is a cycloalkyl group.

The compounds (I) with $R^1$ representing an α- or β-naphthyl group, or an anthracene group also form another subfamily.

Another group of compounds according to the invention comprises the compounds (I) with $R^1$ representing a 2-, 3- or 4-pyridyl, 2- or 3-thienyl and 2- or 3-furyl group.

The compounds (I) with $R^1$ representing

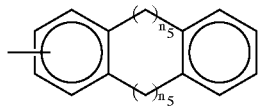

also form another subgroup according to the invention.

For all the subfamilies mentioned above, the substituents not specified may vary according to their respective general definitions.

A particularly preferred group of compounds according to the invention consists of the compounds corresponding to the following formula (V):

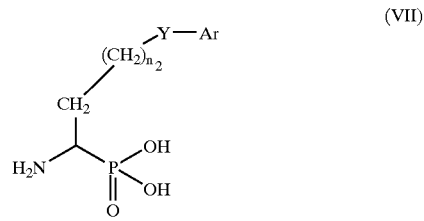

(V)

in which X, $n_2$, Y, $R^1$, $R^8$ and $R^9$ have the above meaning.

The preferences previously indicated for the compounds of formula (I) also apply to those of formula (V).

A group which is even more particularly, preferred comprises the compounds corresponding to the following formula (VI):

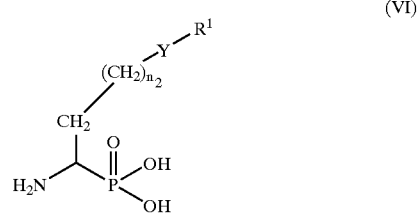

(VI)

in which $n_2$, Y and $R^1$ have the meaning indicated above.

The particular choices mentioned for the compounds of formula (I) from the point of view of the symbols Y and $R^1$ also apply to the compounds of formula (VI).

Among these compounds, those corresponding to the following formula (VII):

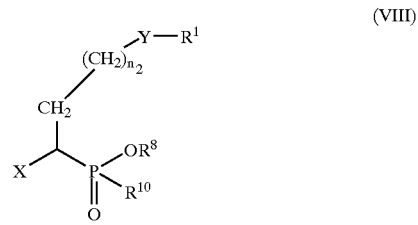

(VII)

where Y and $n_2$ are as defined above and Ar symbolizes $R^1$ representing a phenyl group iv) optionally substituted as defined above or $R^1$ representing a group vii) —$A^2$—$(CH_2)_{n4}$—$A^1$, $A^2$ being a phenyl group (b) optionally substituted as defined above, are particularly preferred.

Another group of compounds according to the second aspect of the present invention comprises the compounds corresponding to the following formula (VIII):

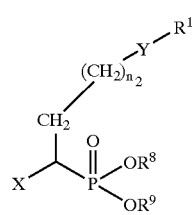

(VIII)

where X, Y, $n_2$, $R^1$, $R^8$ and $R^{10}$ have the above meaning.

The preferences indicated above for the compounds of formula (I) also apply to those of formula (VIII).

A third aspect of the invention relates more particularly to the compounds of formula (I) where Z represents the group

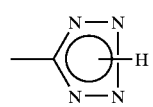

A fourth aspect of the invention more particularly relates to the compounds of formula (I) where Z represents an —$SO_3H$, —$SO_2NHR^{11}$ or —$CONHSO_2R^{11}$ group.

Among the compounds of the present invention, the following are particularly preferred:

1) (S)-O-4-benzylphenoxyserine hydrochloride

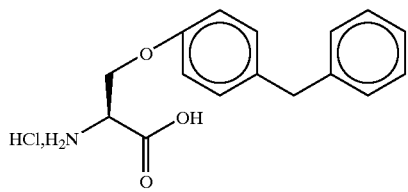

2) 2-(RS)-amino-6-(4-benzylphenoxy)hexanoic acid hydrobromide

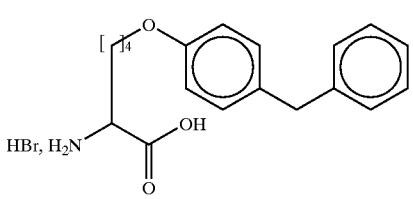

3) 2-(RS)-amino-5-(4-benzylphenoxy)pentanoic acid hydrobromide

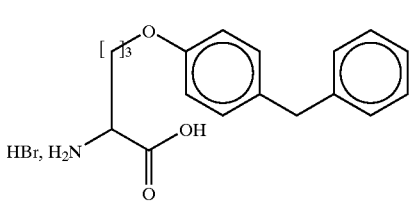

4) 2-(RS)-amino-5-(4-phenoxyphenoxy)pentanoic acid hydrobromide

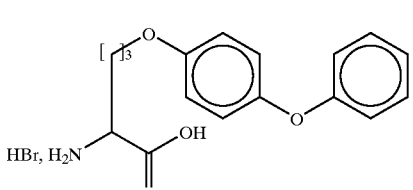

5) 2-(RS)-amino-7-(4-benzylphenoxy)heptanoic acid hydrobromide

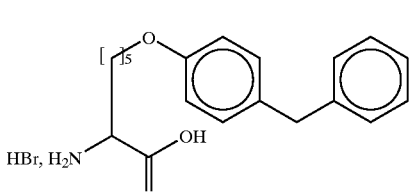

6) 2-(RS)-amino-6-(4-phenylphenoxy)hexanoic acid hydrobromide

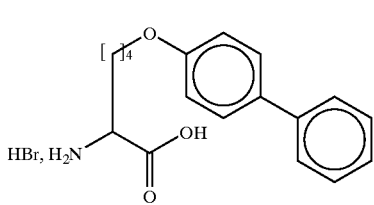

7) 2-(RS)-amino-6-(4-hexyloxyphenoxy)hexanoic acid hydrobromide

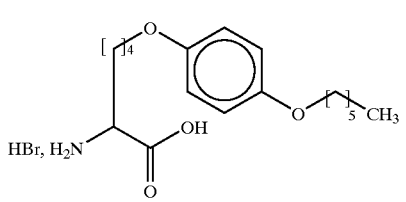

8) 2-(RS)-amino-8-(4-benzylphenoxy)octanoic acid hydrobromide

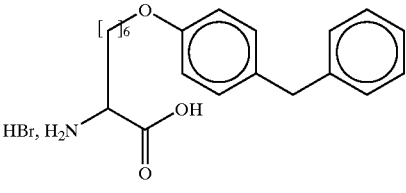

9) 2-(RS)-amino-6-(4-phenoxyphenoxy)hexanoic acid hydrobromide

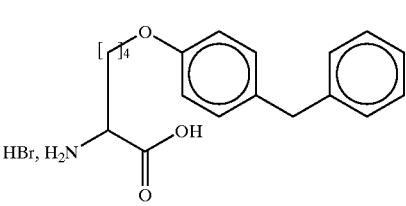

10) 2-(RS)-aminomethyl-6-(4-benzylphenoxy)hexanoic acid

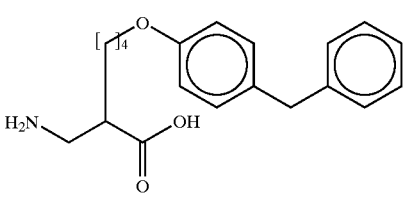

11) 1-(RS)-amino-5-(phenoxy)pentylphosphonic acid hydrobromide

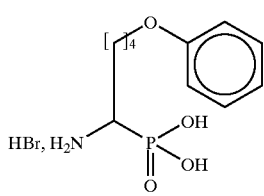

12) 1-(RS)-amino-6-(phenoxy)hexylphosphonic acid hydrobromide

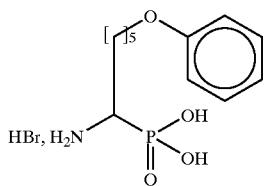

13) 1-(RS)-amino-5-(4-benzylphenoxy)pentylphosphonic acid hydrobromide

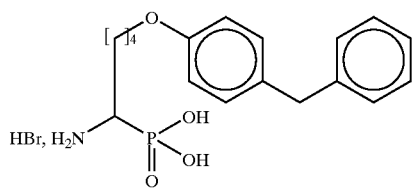

14) 1-(RS)-amino-4-(phenoxy)butylphosphonic acid hydrobromide

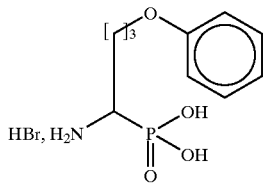

15) 1-(RS)-amino-7-(phenoxy)heptylphosphonic acid hydrobromide

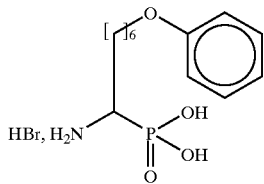

16) 2-(RS)-amino-6-(4-cyclohexylmethylphenoxy)hexanoic acid hydrobromide

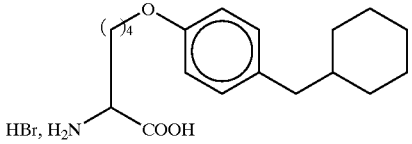

17) 3-(RS)-amino-7-(4-benzylphenoxy)heptanoic acid

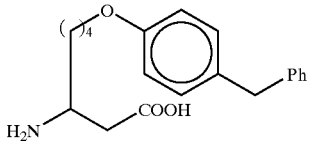

18) 2-(RS)-amino-2-methyl-6-(4-benzylphenoxy)hexanoic acid hydrobromide

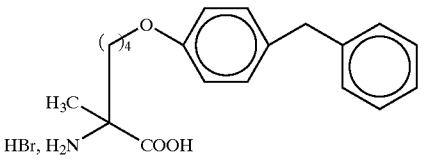

19) 1-(RS)-aminotridecanylphosphonic acid hydrobromide

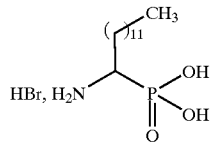

20) 3-(RS)-amino-5-(4-benzylphenoxy)pentahoic acid

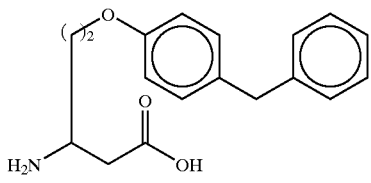

21) 3-(RS)-amino-6-(4-benzylphenoxy)hexanoic acid

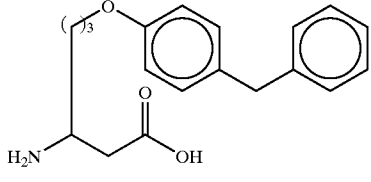

The compounds of formula (I) or (II) as defined above with X representing $NH_2$ and $R^7$ different from a hydrogen atom constitute prodrugs.

The compounds of formula (I) or (II) as defined above with X representing

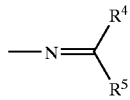

R⁷ being a hydrogen atom constitute prodrugs.

The compounds of formula (I) or (II) as defined above with X representing

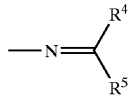

and R⁷ different from a hydrogen atom constitute prodrugs,

The compounds of formula, (I) or (V) as defined above with X representing NH₂ and R⁸ and R⁹ different from a hydrogen atom constitute prodrugs.

The compounds of formula (I) or (V) as defined above where X is NH₂, R⁸ is hydrogen and R⁹ is different from a hydrogen atom constitute prodrugs.

The compounds of formula (I) or (V) as defined above where X is

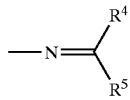

and R⁸ and R⁹ are different from a hydrogen atom constitute prodrugs.

The compounds of formula (I) or (V) as defined above where X is

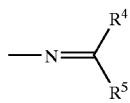

and R⁸ and R⁹ are hydrogen constitute prodrugs.

The compounds of formula (I) or (V) as defined above where X is

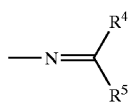

and R⁸ is hydrogen and R⁹ different from a hydrogen atom constitute prodrugs.

The compounds of formula (I) or (VIII) as defined above where X is NH₂ and R⁸ is different from a hydrogen atom constitute prodrugs.

The compounds of formula (I) or (VIII) as defined above where X is

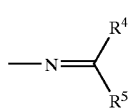

and R⁸ is different from a hydrogen atom constitute prodrugs.

The compounds of formula (I) or (VIII) as defined above where X is

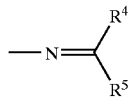

and R⁸ is hydrogen constitute prodrugs.

Examples of prodrugs according to the invention are:

22) ethyl 2-(RS)-amino-7-(4-benzylphenoxy)heptanoate hydrochloride

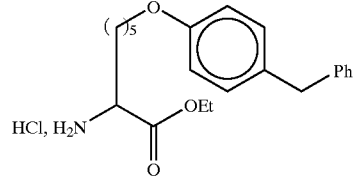

23) ethyl 2-(RS)-amino-6-(4-benzylphenoxy)hexanoate hydrochloride

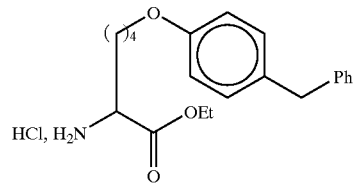

24) diphenyl 1-amino-5-phenoxypentylphosphonate hydrobromide

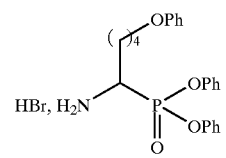

25) ethyl-hydrogen-1-amino-5-phenoxypentylphosphonate hydrobromide

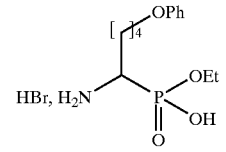

The compounds of the present invention may be prepared from easily available raw materials according to one of the methods indicated below.

The reaction schemes given below describe methods which maybe used for the preparation of the compounds of formula (I), indicating the starting materials, the intermediates as well as the synthesis conditions.

The abbreviations used in the present description correspond to the definitions below:

Ac: acetyl
Bn: benzyl
DIAD: diisopropyl azodicarboxylate
DMF: dimethylformamide

DPPA: diphenylphosphoryl azide
Et: ethyl
EtOH: ethyl alcohol
Et$_2$O: ethyl ether
Me: methyl
NBu$_4$F: tetrabutylammonium fluoride
Pd/C: palladium on carbon
Ph: phenyl
THF: tetrahydrofuran
PCC: pyridinium chlorochromate Schemes 1 to 5 describe the preparation of substituted amino acids.

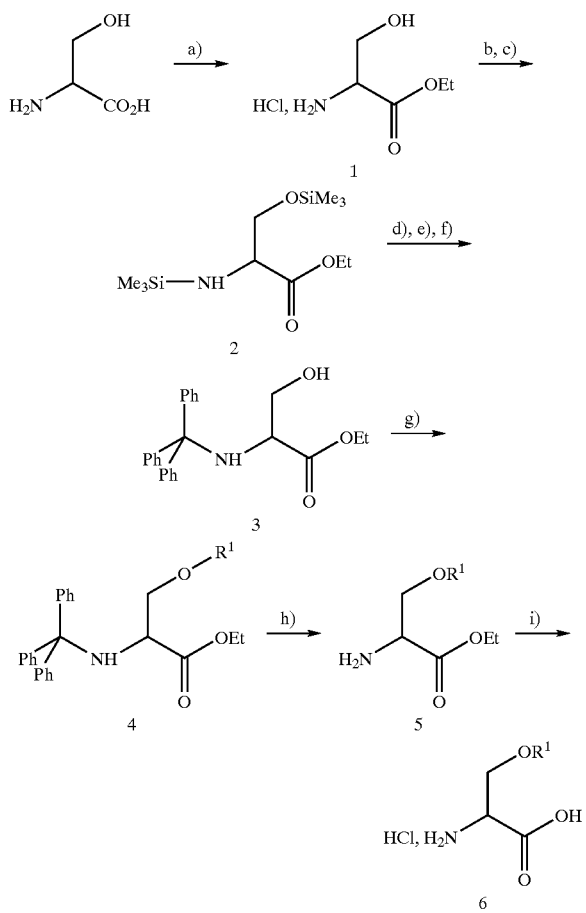

a) SOCl$_2$, EtOH, reflux
b) NEt$_3$, Et$_2$O, CHCl$_3$
c) Me$_3$SiCl, NEt$_3$
d) MeOH
e) Et$_3$N/(Ph)$_3$CCl
f) NBu$_4$f 1M/THF
g) PPh$_3$, DEAD or DIAD, R$^1$OH
h) HCO$_2$H; NaHCO$_3$
i) NaOH N; HCl 2N.

The serine is esterified in the presence of thionyl chloride and EtOH. The amino ester hydrochloride 1 obtained is treated with triethylamine and then with trimethylsilyl chloride in the presence of NEt$_3$ to give the compound 2. The amino functional group is deprotected using anhydrous MeOH and then reprotected by reacting with trityl chloride. The hydroxyl functional group is then released using tetrabutylammonium fluoride to give the compound 3. The hydroxyl functional group of the compound 3 is substituted according to a Mitsunobu-type reaction with a phenolic derivative of formula R$^1$OH to give the compound 4. The compounds 5 are obtained by deprotection with formic acid followed by a treatment using sodium hydrogen carbonate. The amino acid hydrochloride 6 is obtained by saponification in NaOH of the compound 5 followed by acidification in 2N HCl.

The amino acid derivatives 13 and 15 are prepared from the malonates 10 which are obtained either from commercial halides, or from halides 9.

Scheme 2 describes the preparation of noncommercial halides 9.

Scheme 2

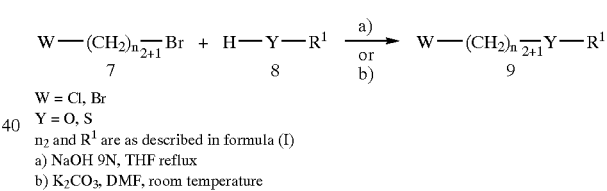

W = Cl, Br
Y = O, S
n$_2$ and R$^1$ are as described in formula (I)
a) NaOH 9N, THF reflux
b) K$_2$CO$_3$, DMF, room temperature The compounds 9 may be obtained according to two routes:
  by treatment in 9N sodium hydroxide under reflux in the presence of THF or by the use of powdered K$_2$CO$_3$ in the DMF at room temperature.

Scheme 3 describes the synthesis of salts of amino esters 13 and of amino acids 15.

Scheme 3

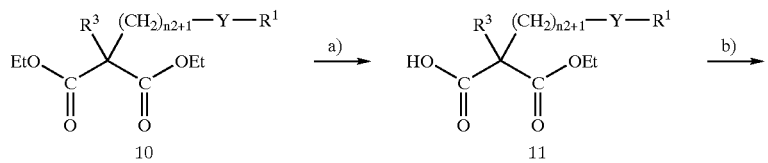

R³, n₂, Y and R¹ are as defined in formula (I).
a) KOH, EtOH, 0° C.
b) DPPA, NEt₃, toluene, benzyl alcohol, 80° C.
c) H₂, Pd/C, EtOH
d) HCl 3N
e) NaOH, MeOH; HCl N
f) HBr/CH₃CO₂H The malonates of formula 10 are obtained by alkylation of a malonate with the corresponding brominated or chlorinated derivatives 9 in the presence of sodium ethoxide in ethanol under reflux. Monosaponification using a solution of KOH in EtOH gives compounds 11 which are subjected to a Curtius reaction in the presence of DPPA, NEt₃ and benzyl alcohol in toluene at 80° C. overnight.

The benzyloxycarbonyl functional group is deprotected by catalytic hydrogenation in ethanol using Pd/C to give the amino esters 13. Saponification of the compounds 12 using a solution of NaOH in MeOH gives the derivatives 14 which are subjected to the action of HBr in acetic acid to give the amino acids 15.

The amino acid derivatives 18 and 19 are prepared from the malonates 10 (with R³=H) described in scheme 3.

Scheme 4 describes the synthesis of the amino ester salts 19 and of the amino acids 18.

Scheme 4 a) NaOH 6N, reflux
b) paraformaldehyde, HNEt₂ ACOEt
c) NH₂OH HCl, NaOEt/EtOH
d) SOCl₁, R⁷OH The acrylic acids 17 are prepared via the diacids 16 obtained by saponification in 6N sodium hydroxide under reflux, and then a Mannich reaction in the presence of paraformaldehyde, diethylamine in ethyl acetate under reflux.

The derivatives 18 are obtained by addition of hydroxylamine in the presence of sodium ethoxide on the acrylic acids 17 under reflux. The amino ester salts 19 are prepared from the derivatives 18 by reaction in the presence of thionyl chloride in an alcohol R⁷OH.

Scheme 5 shows the preparation of β-amino acids 24 and of amino acid salts 25 from malonates.

Scheme 5

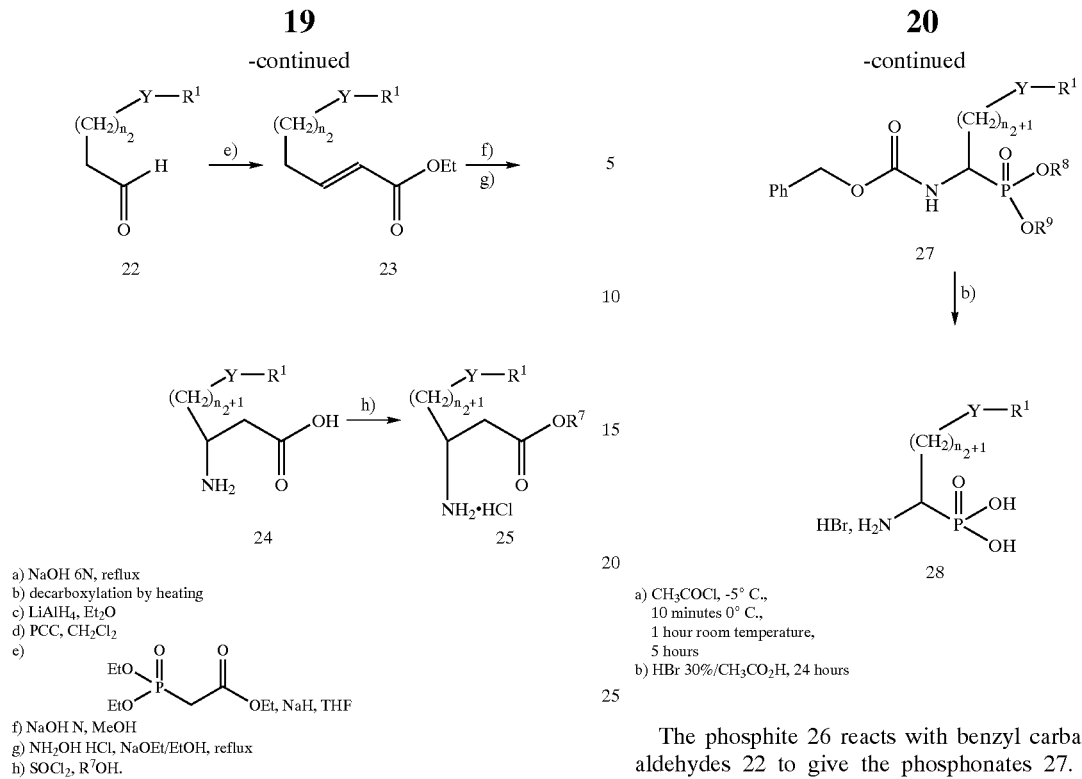

a) NaOH 6N, reflux
b) decarboxylation by heating
c) LiAlH$_4$, Et$_2$O
d) PCC, CH$_2$Cl$_2$
e)

f) NaOH N, MeOH
g) NH$_2$OH HCl, NaOEt/EtOH, reflux
h) SOCl$_2$, R$^7$OH.

The malonates of formula 20 are obtained by alkylation of a malonate with the corresponding brominated or chlorinated derivatives in the presence of sodium ethoxide in ethanol under reflux. The acids 21 are prepared via the diacids obtained by saponification in 6N sodium hydroxide under reflux, and then a heat decarboxylation. After reduction using lithium aluminum hydride followed by oxidation with pyridinium chlorochromate (PCC), the aldehyde 22 is obtained. The amino acids 24 are prepared via a Wittig Horner reaction using triethylphosphonoacetate followed by saponification in the presence of normal sodium hydroxide and then the addition of hydroxylamine in the presence of sodium ethoxide onto the acrylic derivatives.

The amino ester salts 25 are prepared from the derivatives 24 by reaction in the presence of thionyl chloride in an alcohol R$^7$OH.

Schemes 6 and 7 describe the preparation of the aminophosphonic derivatives 28.

The aminophosphonic derivatives 28 are obtained according to two routes:

Route A (scheme 6)

Scheme 6

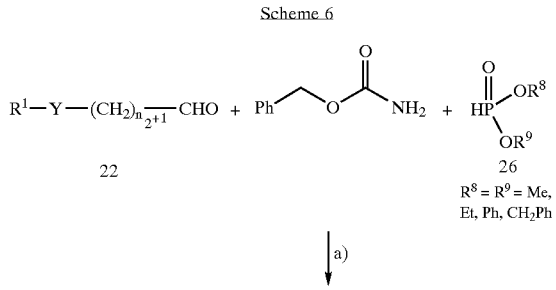

a) CH$_3$COCl, -5° C.,
   10 minutes 0° C.,
   1 hour room temperature,
   5 hours
b) HBr 30%/CH$_3$CO$_2$H, 24 hours The phosphite 26 reacts with benzyl carbamate and the aldehydes 22 to give the phosphonates 27. Deprotection using 30% HBr in acetic acid makes it possible to obtain the derivatives 28.

Route B (scheme 7):

Scheme 7

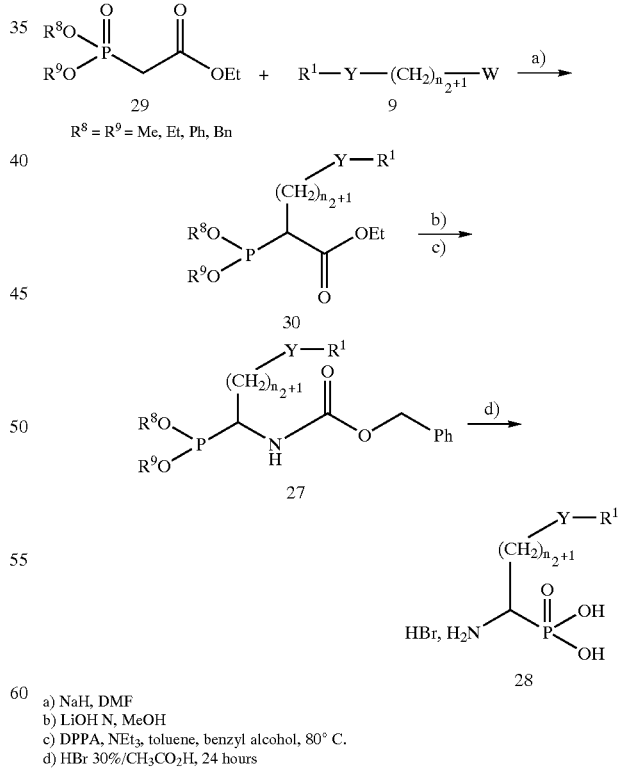

a) NaH, DMF
b) LiOH N, MeOH
c) DPPA, NEt$_3$, toluene, benzyl alcohol, 80° C.
d) HBr 30%/CH$_3$CO$_2$H, 24 hours The phosphonoacetates 29 are alkylated with the halogenated derivatives 9 using NaH in DMF. After saponification and Curtius reaction, the phosphonates 27 are obtained.

Deprotection using 30% HBr in acetic acid makes it possible to obtain the derivatives 28.

Scheme 8 describes the preparation of the aminophosphonic derivatives 31 and 33.

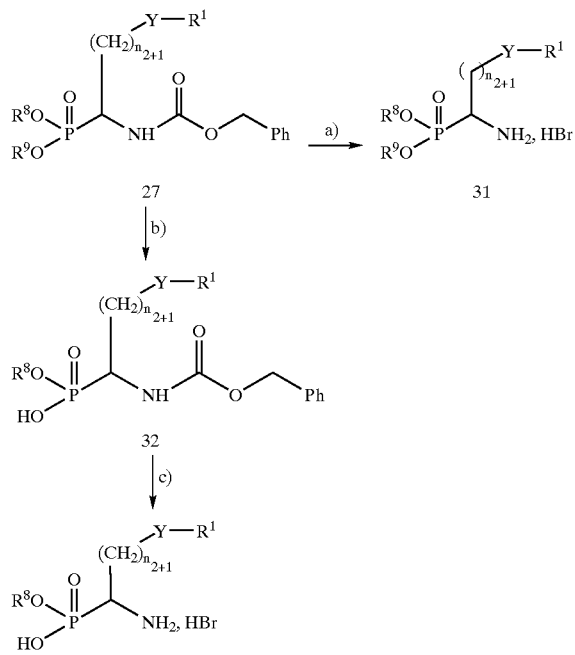

a) HBr, CH$_3$COOH, 1 hour
b) NaOH 2N, NBu$_4$Br
c) HBr 30%/CH$_3$COOH, 1 hour.

The compound 27 is subjected to the action of a 30% HBr solution in acetic acid to give the product 31.

The compound 33 is obtained in two stages from the derivatives 27: monosaponification in the presence of a phase transfer agent in 2N NaOH and then deprotection with 30% HBr in acetic acid.

The inventors have shown that the compounds (I) according to the invention and in particular the compounds corresponding more particularly to one of the formulae (II) to (VIII), have LTA$_4$ hydrolase inhibiting properties.

They possess an advantageous therapeutic activity, in particular in the field of anti-inflammatory treatments.

They also possess an advantageous antiarthritic activity.

The compounds of the invention also have antipsoriatic properties.

Moreover, the inventors have shown that the compounds of the invention prevent the increase in the tissue levels of LTB$_4$ which is induced by cyclooxygenase inhibitors.

They are thus useful for the prevention of certain paradoxical pro-inflammatory side effects of cyclooxygenase inhibitors.

Finally, LTB$_4$ being the endogenous ligand for the receptor inducing proliferation of the peroxisomes, the compounds of the invention also find applications in the fields of hepatoprotection and antimitotic action.

The subject of the present invention is thus also the use of the compounds of formula (I) and in particular the compounds corresponding more particularly to one of the formulae (II) to (VIII), as medicaments which act as inhibitors of the activity of LTA$_4$ hydrolase, in particular for an anti-inflammatory or antiarthritic treatment.

Its subject is also the use of the compounds of the invention as antipsoriatic medicaments.

Its subject is also their use as hepatoprotective or antimitotic medicaments.

Its subject is also the use of such compounds as medicaments intended for the treatment of an overproduction of LTB$_4$, induced in particular by cyclooxygenase inhibitors.

Its subject is also the use of such compounds (I) and in particular the compounds corresponding more particularly to one of the formulae (II) to (VIII), for the preparation of medicaments intended for inhibiting the activity of LTA$_4$ hydrolase.

Its subject is in particular their use for the preparation of medicaments intended for the abovementioned treatments.

The compounds of formula (I) and in particular the compounds corresponding more particularly to one of the formulae (II) to (VIII), may be administered in a physiologically acceptable vehicle or excipient.

Accordingly, the subject of the present invention is also pharmaceutical compositions comprising a therapeutically effective quantity of at least one compound of formula (I) in combination with a physiologically acceptable vehicle or excipient.

The compounds (I) and in particular the compounds corresponding more particularly to one of the formulae (II) to (VIII), of the invention may also be used in combination with cyclooxygenase inhibitors.

The invention thus relates to medicaments or pharmaceutical compositions containing a therapeutically effective quantity of a compound (I) and in particular the compounds corresponding more particularly to one of the formulae (II) to (VIII), and a therapeutically effective quantity of a cyclooxygenase inhibiting compound, optionally in combination with a physiologically acceptable vehicle or excipient.

Examples of cyclooxygenase inhibitors useful according to the invention are aspirin (acetylsalicylic acid), ibuprofen and diclofenac.

The medicaments or pharmaceutical compositions according to the invention may be advantageously administered by the local cutaneous or ocular routes, by the parenteral route or by the oral route, the latter being preferred.

The subject of the invention is also a method of treatment for inhibiting the activity of LTA$_4$ hydrolase in humans.

Its subject is also such a method for the treatments indicated above.

Its subject is also a method of treating an overproduction of LTB$_4$, in particular induced by cyclooxygenase inhibitors.

Other advantages and characteristics of the present invention will emerge on reading the examples of preparation of compounds of formula (I) given by way of nonlimiting illustration, as well as the biological results given below.

EXAMPLES

A summary table of the examples of compounds of formula (I) is given below:

Summary Table

| Ex | X | $n_1$ | $R^2$ | $R^3$ | $n_2$ | Y | $R^1$ | $n_3$ | Z |
|---|---|---|---|---|---|---|---|---|---|
| 5 | —$NH_2$ | 0 | H | H | 0 | —O— | —$C_6H_4$—(4-$CH_2$Ph) | 0 | —COOH |
| 51 | —$NH_2$ | 0 | H | H | 3 | —O— | —$C_6H_4$—(4-$CH_2$Ph) | 0 | —COOH |
| 52 | —$NH_2$ | 0 | H | H | 2 | —O— | —$C_6H_4$—(4-$CH_2$Ph) | 0 | —COOH |
| 53 | —$NH_2$ | 0 | H | H | 2 | —O— | —$C_6H_4$—(4-OPh) | 0 | —COOH |
| 54 | —$NH_2$ | 0 | H | H | 4 | —O— | —$C_6H_4$—(4-$CH_2$Ph) | 0 | —COOH |
| 55 | —$NH_2$ | 0 | H | H | 3 | —O— | —$C_6H_4$—(4-Ph) | 0 | —COOH |
| 56 | —$NH_2$ | 0 | H | H | 3 | —O— | —$C_6H_4$—(4-O($CH_2$)$_5$$CH_3$) | 0 | —COOH |
| 57 | —$NH_2$ | 0 | H | H | 5 | —O— | —$C_6H_4$—(4-$CH_2$Ph) | 0 | —COOH |
| 58 | —$NH_2$ | 0 | H | H | 3 | —O— | —$C_6H_4$—(4-OPh) | 0 | —COOH |
| 61 | —$NH_2$ | 1 | H | H | 3 | —O— | —$C_6H_4$—(4-Ph) | 0 | —COOH |
| 67 | —$NH_2$ | 0 | H | H | 3 | —O— | —Ph | 0 | —PO(OH)$_2$ |
| 80 | —$NH_2$ | 0 | H | H | 4 | —O— | —Ph | 0 | —PO(OH)$_2$ |
| 81 | —$NH_2$ | 0 | H | H | 3 | —O— | —$C_6H_4$—(4-$CH_2$Ph) | 0 | —PO(OH)$_2$ |
| 82 | —$NH_2$ | 0 | H | H | 2 | —O— | —Ph | 0 | —PO(OH)$_2$ |
| 83 | —$NH_2$ | 0 | H | H | 5 | —O— | —Ph | 0 | —PO(OH)$_2$ |
| 85 | —$NH_2$ | 0 | H | H | 3 | —O— | —$C_6H_4$-(4-$CH_2$—cyclohexyl) | 0 | —COOH |
| 91 | —$NH_2$ | 0 | H | H | 3 | —O— | —$C_6H_4$—(4-$CH_2$Ph) | 1 | —COOH |
| 93 | —$NH_2$ | 0 | H | $CH_3$ | 3 | —O— | —$C_6H_4$—(4-$CH_2$Ph) | 0 | —COOH |
| 100 | —$NH_2$ | 0 | H | H | 9 | —$CH_2$— | $CH_3$ | 0 | —PO(OH)$_2$ |
| 42 | —$NH_2$ | 0 | H | H | 4 | —O— | —$C_6H_4$—(4-$CH_2$Ph) | 0 | —COOEt |
| 94 | —$NH_2$ | 0 | H | H | 3 | —O— | —$C_6H_4$—(4-$CH_2$Ph) | 0 | —COOEt |
| 96 | —$NH_2$ | 0 | H | H | 3 | —O— | —Ph | 0 | —PO(OPh)$_2$ |
| 98 | —$NH_2$ | 0 | H | H | 3 | —O— | —Ph | 0 | —PO(OH)(OEt) |
| 105 | —$NH_2$ | 0 | H | H | 1 | —O— | —$C_6H_4$—(4-$CH_2$Ph) | 1 | —COOH |
| 114 | —$NH_2$ | 0 | H | H | 2 | —O— | —$C_6H_4$—(4-$CH_2$Ph) | 1 | —COOH |

Example 1

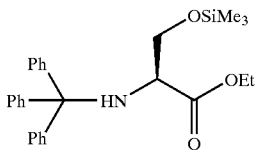

11.98 g (90 mmol) of ethyl serinate, in hydrochloride form, are dissolved in 155 ml of $CH_2Cl_2$. 22.78 g (209.68 mmol) of trimethylsilyl chloride are added under an inert atmosphere.

The medium is heated under reflux for 20 minutes and then the temperature is allowed to return to room temperature. 21.2 g (209.90 mmol) of triethylamine in 60 ml of $CH_2Cl_2$ are then added and the medium is heated under reflux for 45 minutes.

The medium is then cooled to 0° C. and a solution of 5.9 ml (135 mmol) of anhydrous methanol in 22 ml of $CF_2Cl_2$ is added.

The temperature of the medium is allowed to rise to room temperature and 9.1 g (90 mmol) of $NEt_3$ and 25 g (90 mmol) of trityl chloride are successively added and the medium is stirred overnight at room temperature.

The medium is concentrated under vacuum and taken up in 200 ml of $Et_2O$. It is washed with water (once 30 ml).

The medium is dried over $MgSO_4$, filtered and concentrated under vacuum.

38.8 g of the desired compound are obtained.

Example 2

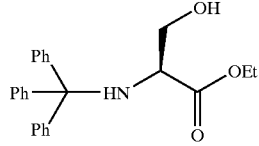

50 ml of a molar solution of tetrabutylammonium fluoride ($NBu_4F$) in THF are added, at room temperature, to a solution of 38.8 g of the product of Example 1 in 53 ml of THF. The medium is stirred for 10 minutes at room temperature.

500 ml of $Et_2O$ are then added and the organic phase is successively washed with a saturated aqueous sodium hydrogen carbonate solution (twice 60 ml) and then a saturated aqueous sodium thiosulfate solution (twice 60 ml). The organic phase is dried over $MgSO_4$, filtered and concentrated under vacuum. The oily residue obtained is purified by flash chromatography using the petroleum ether/$Et_2O$ (1/1) mixture and then $Et_2O$ as eluents.

Example 3

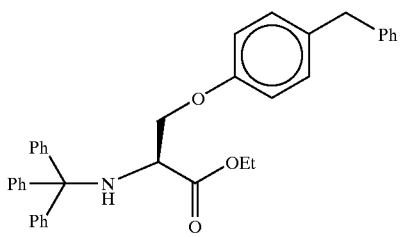

4.8 g (1.07 equivalents) of triphenylphosphine and 4.65 g (1.46 equivalents) of 4-phenylphenol are successively added to a solution of 6.5 g (17.2 mmol) of amino ester of Example 2 in 200 ml of toluene. The reaction medium is vigorously stirred for 5 minutes, and then 3.70 g (1.07 equivalents) of diisopropyl azodicarboxylate are added.

The reaction medium is stirred overnight at room temperature, filtered and evaporated to dryness. The oily residue is purified by flash chromatography using the ether-petroleum ether (5/95) mixture as eluent. 6.6 g (12.15 mmol) of the desired compound are thus obtained.

Example 4

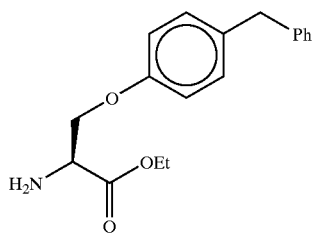

6.6 g (12.15 mmol) of amino ester of Example 3 are vigorously stirred for 5 hours at room temperature in the presence of 85 ml of formic acid. The reaction medium is then evaporated to dryness, and a white solid is obtained which is taken up in 100 ml of water. The aqueous phase is washed with Et$_2$O (3 times 20 ml) and is then basified using sodium hydrogen carbonate. The basic aqueous phase is then extracted with ethyl acetate (3 times 20 ml). The organic phase is dried over MgSO$_4$, filtered and concentrated under vacuum. 1.86 g (6.6 mmol) of the desired compound are obtained.

Example 5

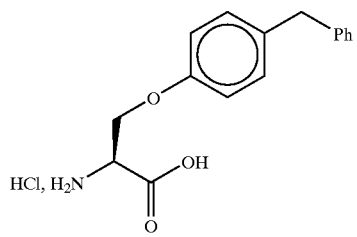

1.86 (6.2 mmol) of product of Example 4 are mixed with 6.5 ml of N NaOH and the medium is stirred overnight at room temperature.

The aqueous phase is washed with ethyl ether (once 10 ml) and then concentrated under vacuum. 15 ml of HCl N are then added. The white solid obtained is filtered, washed with water and dried under vacuum over P$_2$O$_5$.

1.26 g (3.75 mmol) of amino acid hydrochloride are obtained. (Melting=225° C.).

The $^1$H NMR is in agreement with the chemical structure.

Example 6 (method a)

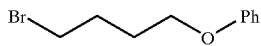

17.41 g (185.25 mmol) of phenol, 14.5 ml of THF and 62 ml of 9N NaOH are introduced into a round-bottomed flask.

40 g (185.25 mmol) of 1,4-dibromobutane are added dropwise.

The medium is heated under reflux for 45 minutes. organic phase is washed with 30 ml of water, dried over MgSO$_4$, filtered and concentrated. The oily residue is distilled under vacuum produced by a slide vane rotary vacuum pump. The fraction distilling at 80–105° C. is recovered under 1 mm of Hg.

15.96 g (37%) of a colorless oil are obtained.

Example 7 (method b)

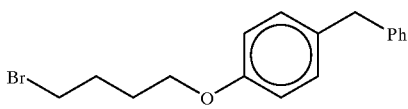

11 g (60 mmol) of 4-hydroxydiphenylmethane, 64.8 g (300 mmol) of 1,4-dibromobutane, 41.5 g (300 mmol) of powdered K$_2$CO$_3$ and 94 ml of anhydrous DMF are successively introduced into an Erlenmeyer flask.

The medium is stirred overnight at room temperature. It is filtered and the filtrate is taken up in 300 ml of ethyl acetate. The organic phase is washed with a saturated aqueous NaCl solution (3 times 100 ml), dried over MgSO$_4$, filtered and concentrated.

The excess 1,4-dibromobutane is distilled off under vacuum. 18 g (56.5 mmol) of oily residue corresponding to the desired product are obtained.

Examples 8 to 17 are prepared according to one of the methods (a or b) described above.

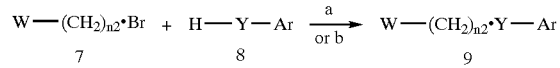

Example 18

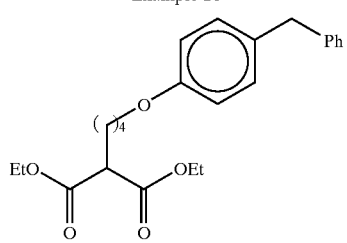

A sodium ethoxide solution prepared from 1.27 g (55.21 mmol) of sodium in 32 ml of EtOH is added to a mixture of 14.3 g (89.37 mmol) of diethyl malonate and 6.78 g (21.27 mmol) of the brominated derivative of Example 7. The medium is heated under reflux for 4 hours.

The medium is concentrated under vacuum, and the residue is taken up in water and extracted with $Et_2O$.

The ethereal phase is washed 3 times with water, dried over $MgSO_4$, filtered and then concentrated. The excess diethyl malonate is removed by vacuum distillation.

6.4 g (yield 76%) of yellow oil are obtained.

Examples 19 to 25 are prepared according to the same procedure as that described in Example 18.

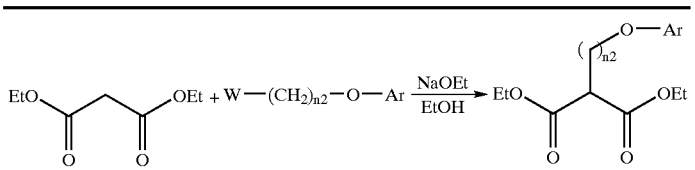

| Ex. No. | W—$(CH_2)_{n2}$—O—Ar | product |
|---|---|---|
| 19 | ex 8 | 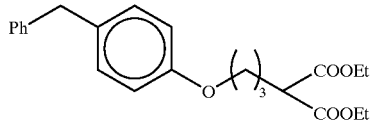 |
| 20 | ex 11 | 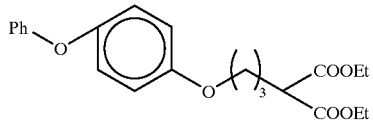 |
| 21 | ex 9 | 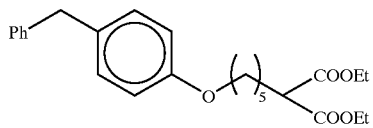 |
| 22 | ex 13 | 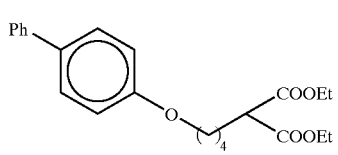 |
| 23 | ex 14 | 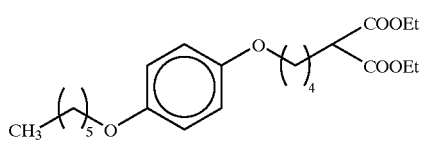 |
| 24 | ex 10 | 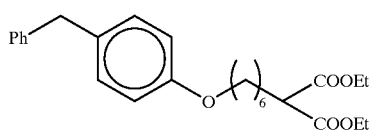 |
| 25 | ex 12 | 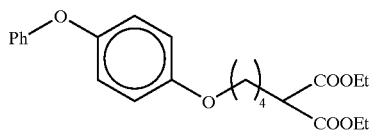 |

Example 26

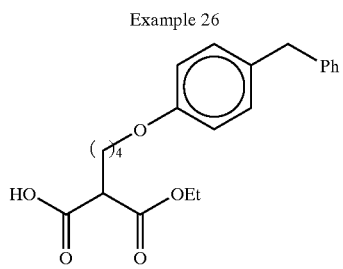

A solution of 1.09 g (16.51 mmol) of potassium hydroxide in 16 ml of EtOH is added at 0° C. to a solution of 6.4 g (16.08 mmol) of diester of Example 18 in 3 ml of EtOH.

The medium is stirred overnight at 0° C.

The medium is then concentrated. The residue is taken up in 100 ml of water and washed with Et$_2$O (twice 30 ml). The aqueous phase is cooled and then acidified with a concentrated hydrochloric acid solution. The aqueous phase is extracted with ether (twice 40 ml). The ethereal phases are combined, dried over MgSO$_4$, filtered and concentrated. 4.71 g (79%) of a very viscous yellow oil are thus obtained.

Examples 27 to 33 are prepared according to the same method as that described in Example 26.

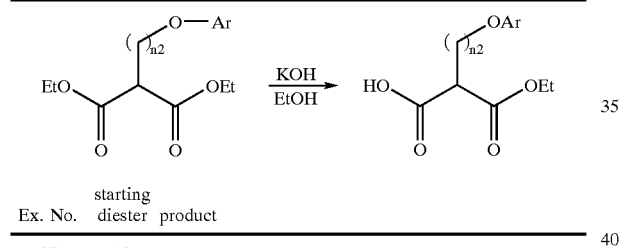

| Ex. No. | starting diester | product |
|---|---|---|
| 27 | 19 | 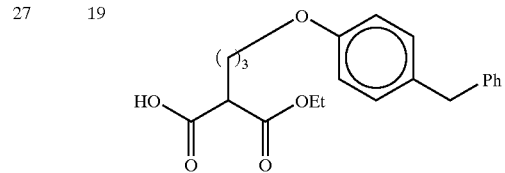 |
| 28 | 20 | 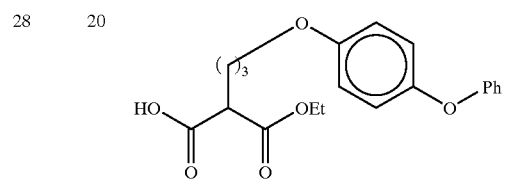 |
| 29 | 21 | 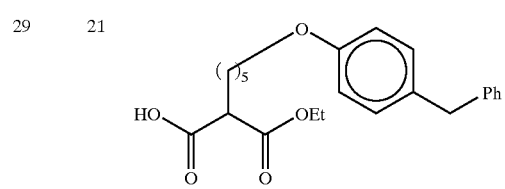 |

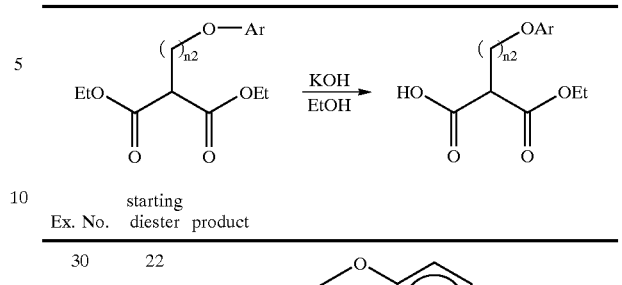

| Ex. No. | starting diester | product |
|---|---|---|
| 30 | 22 | |
| 31 | 23 | |

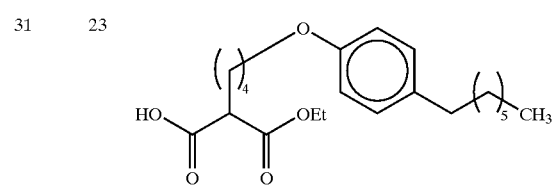

Example 34

3.67 g (13.33 mmol) of DPPA are added dropwise, followed by 1.34 g (13.33 mmol) of NEt$_3$ to a solution of 4.71 g of the monoacid of Example 26 in 20 ml of toluene. The medium is heated at 80° C. for 1 hour. The medium is allowed to return to room temperature and 1.65 g (15.27 mmol) of benzyl alcohol are added and the medium is heated at 80° C. overnight. The toluene phase is successively washed with water (once 10 ml), with a saturated aqueous sodium hydrogen carbonate solution (once 10 ml) and with water (once 5 ml). The organic phase is dried over MgSO$_4$, filtered and concentrated under vacuum.

6.5 g of crude product are thus obtained. The latter is purified by flash chromatography on silica with the ethyl ether-petroleum ether (3/7) mixture as eluent. 4.55 g (9.55 mmol; yield=75%) of carbamate (colorless oil) are obtained.

Examples 35 to 41 are prepared according to the same method as that described for Example 34.

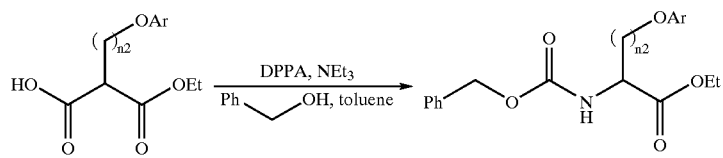

Example 42

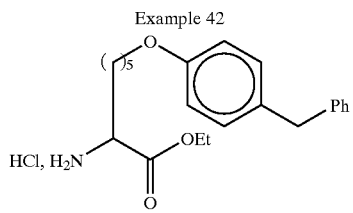

1 g (2.04 mmol) of the carbamate of Example 37 is dissolved in 20 ml of EtOH. 100 mg of 10% Pd/C are then added and then the medium is hydrogenated at a pressure of about 1 bar overnight at room temperature.

The suspension is filtered on celite and then a evaporated to dryness. The oily residue is taken up in a concentrated aqueous HCl solution. The acidic aqueous phase is washed with $Et_2O$ (twice 20 ml). The aqueous phase is evaporated to dryness and the residue is dried under vacuum over $P_2O_5$ to a constant mass. 0.64 g (yield 80%) of a white solid is thus obtained. The $^1H$ NMR is in agreement with the chemical structure.

Example 43

11.5 ml of an N NaOH solution are added to a solution of 4.55 g (9.55 mmol) of the ester of Example 34 in 20 ml of MeOH. The medium is kept stirred overnight.

The MeOH is evaporated off under vacuum and then the residual aqueous phase is washed with ethyl ether (twice 15 ml).

The basic aqueous phase is cooled to about 5° C., is acidified to pH=1 with a N HCl solution and is extracted with ethyl ether (twice 20 ml). After drying over $MgSO_4$, filtration and concentration under vacuum, 3.33 g (78%) of a white solid are obtained.

Examples 44 to 50 are prepared according to the same procedure as that described for Example 43.

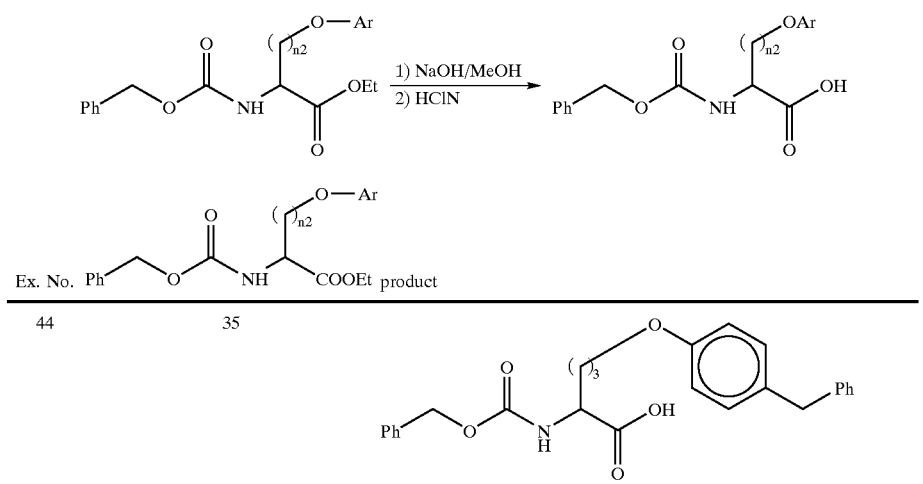

| Ex. No. | | product |
|---|---|---|
| 44 | 35 | 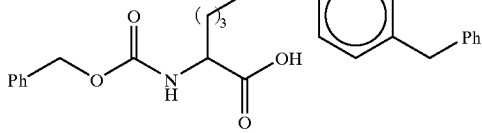 |
| 45 | 36 | 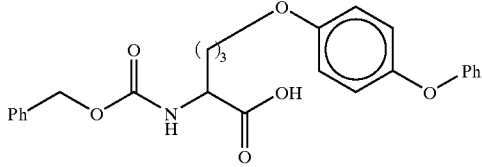 |
| 46 | 37 | 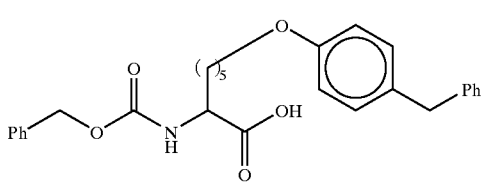 |

-continued

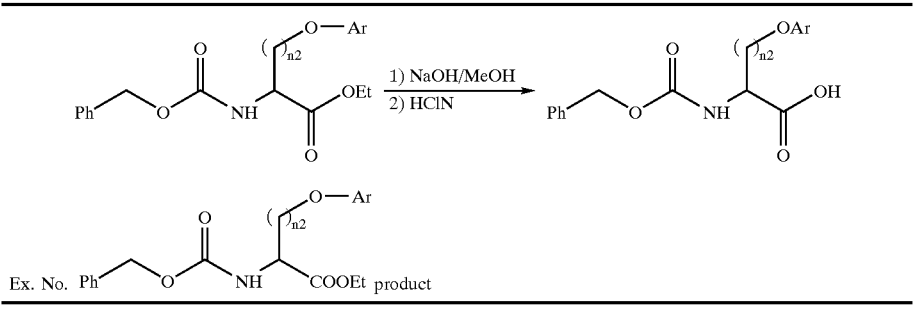

| Ex. No. | product |
|---|---|
| 47 | 38 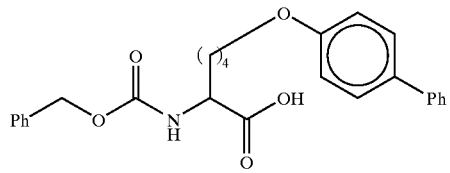 |
| 48 | 39 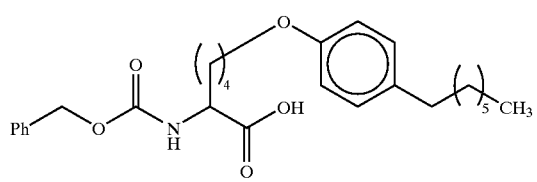 |
| 49 | 40 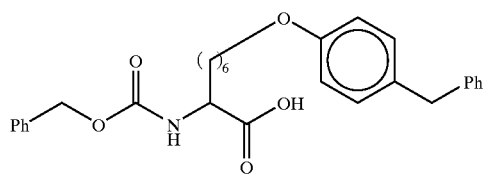 |
| 50 | 41 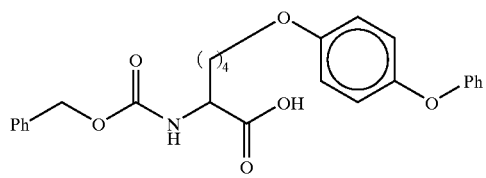 |

Example 51

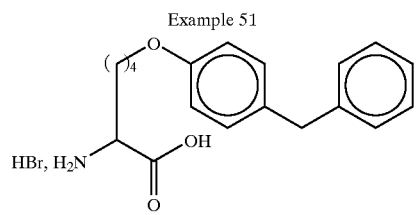

0.89 g (1.99 mmol) of the carbamate of Example 43 and 5 ml of a saturated gaseous HBr solution in acetic acid are introduced into a round-bottomed flask. The stirring is maintained for 2 hours.

The acetic acid is evaporated off under vacuum and the oily residue is triturated in anhydrous ethyl ether. The medium is filtered and washed with ethyl ether. The white solid is dried under vacuum over $P_2O_5$. 0.52 g (66%) of the desired amino acid is obtained (melting >200° C.).

The $^1$H NMR is in agreement with the chemical structure.

Examples 52 to 58 are prepared according to the same procedure as that described in Example 51.

| Ex. No. | | Product | Melting ° C. |
|---|---|---|---|
| 57 | 49 | (structure: n=6, OAr = O-C6H4-CH2-C6H5) | 120 |
| 58 | 50 | (structure: n=4, OAr = O-C6H4-O-C6H5) | 130 |
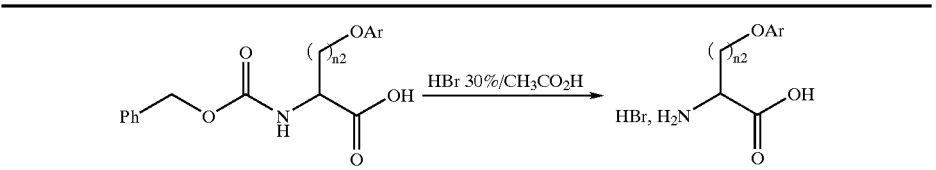
| Ex. No. | | Product | Melting ° C. |
|---|---|---|---|
| 52 | 44 | (structure: n=3, OAr = O-C6H4-CH2-C6H5) | 199 |
| 53 | 45 | (structure: n=3, OAr = O-C6H4-O-C6H5) | 162 |
| 54 | 46 | (structure: n=5, OAr = O-C6H4-CH2-C6H5) | 100 |

-continued

| Ex. No. | Product | | Melting °C. |
|---|---|---|---|
| 55 | 47 | 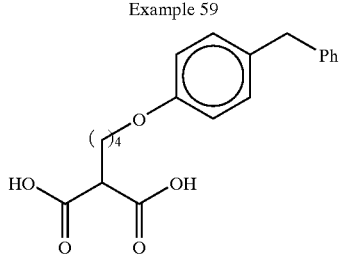 | 185 |
| 56 | 48 | 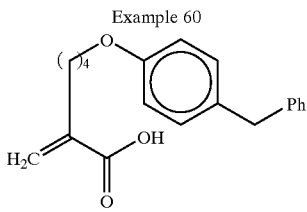 | 135 |

Example 59 of 7.92 g (23.15 mmol) of the malonic diacid of Example 59 in 50 ml of AcOEt. The medium is heated under reflux for 30 minutes.

The solution is then cooled using an ice and water bath, diluted with 10 ml of water and then acidified with a 3N HCl solution to pH=1. The aqueous phase is removed. The organic phase is washed with water (once 10 ml), dried over $MgSO_4$, filtered and concentrated.

6.04 g (84%) of a white solid are obtained.

9.25 g (23.24 mmol) of the malonic diester of Example 18 are diluted with 10 ml of water. 2.32 g (58.00 mmol) of sodium hydroxide pellets are added.

The medium is stirred and heated under reflux for 1 h 30 min.

It is diluted with water and washed with $Et_2O$ (once 15 ml).

The aqueous phase is cooled and acidified with a concentrated aqueous hydrochloric acid solution to pH=1. The medium is extracted with $Et_2O$ (twice 25 ml). The ethereal phases are combined, dried over $MgSO_4$, filtered and concentrated. 7.92 g (100%) of a white solid are obtained.

Example 60

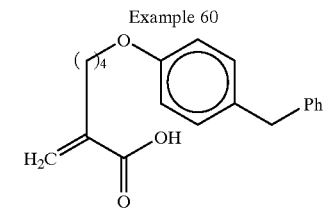

1.69 g (23.15 mmol) of diethylamine and then 1.04 g (30.40 mmol) of paraformaldehyde are added to a solution Example 61

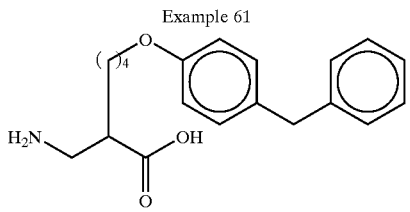

A solution of 0.44 g (19.13 mmol) of sodium in 15 ml of anhydrous EtOH is heated under reflux. 1.35 g (19.42 mmol) of hydroxylamine hydrochloride in 1 ml of hot water are added to this solution. The medium is cooled on ice to 5° C., filtered and the precipitate is washed with 2 ml of anhydrous EtOH.

3 g (9.70 mmol) of acrylic acid of Example 60 are added to the filtrate. The medium is stirred and heated under reflux for 24 hours.

The medium is filtered, washed with water, with EtOH and then with ethyl ether. 0.71 g of a white solid (22%) (melting >200° C.) is obtained. The $^1$H NMR is in agreement with the chemical structure.

Example 62

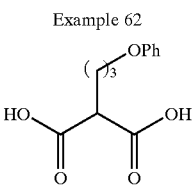

The chlorinated derivative of Example 15 reacts with diethyl malonate according to the same method as that described in Example 18. The malonate thus obtained is saponified according to the same procedure as that described in Example 59 to give the desired compound.

Example 63

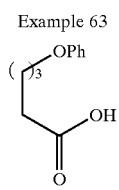

The diacid of Example 62 is decarboxylated by heating to 140° C. until the gaseous emission disappears to give the desired acid.

Example 64

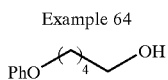

A solution of 31.34 g (161.36 mmol) of acid of Example 63 in 138 ml of anhydrous $Et_2O$ is added to a suspension of 7.35 g (193.67 mmol) of $LiAlH_4$ in 210 ml of anhydrous $Et_2O$. The medium is stirred overnight at room temperature.

It is cooled on ice to 5° C. and 5.25 ml of water, 5.25 ml of 15% NaOH and 15.75 ml of water are added successively. After stirring for 2 hours, the medium is filtered, rinsed with ethyl ether and the filtrate is concentrated.

19.97 g (68%) of alcohol are obtained.

Example 65

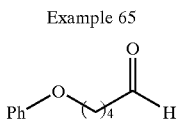

A solution of 19.77 g (110.8 mmol) of the alcohol of Example 64 dissolved in 135 ml of $CH_2Cl_2$ is added to a solution of 48 g (222.67 mmol) of PCC in 220 ml of $CH_2Cl_2$ cooled to 0° C. The medium is stirred for 3 hours at room temperature, filtered on celite, evaporated to dryness and purified by flash chromatography (ethyl ether/heptane 4/6). 9.94 g (55.77 mmol) of aldehyde are obtained.

Example 66

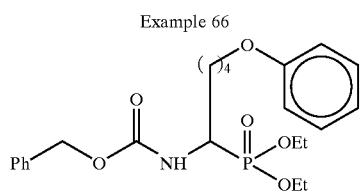

6.75 g (44.6 mmol) of benzyl carbonate, 6.5 g (44.6 mmol) of diethyl phosphite and 33.5 ml of acetyl chloride are mixed. The mixture is cooled to –5° C. and 9.94 g (55.77 mmol) of aldehyde of Example 65 are added dropwise. The mixture is stirred for one hour at 0° C. and then overnight at room temperature.

The excess acetyl chloride is removed by evaporation under vacuum and then the residue is taken up in 50 ml of $CH_2Cl_2$. The medium is successively washed with water (once 30 ml), with a saturated aqueous sodium bisulfite solution (twice 30 ml), with a saturated aqueous $NaHCO_3$ solution (3 times 30 ml) and with water (once 60 ml). The organic phase is dried over $MgSO_4$, filtered and concentrated. 20.19 g of a crude product are obtained, which product is chromatographed on silica (eluent $Et_2O$)

10.93 g (54.5%) of product are thus recovered.

Example 67

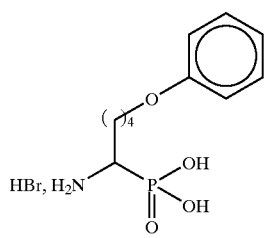

1.3 g (2.4 mmol) of the phosphonate of Example 66 and 3.5 ml of a 30% gaseous HBr solution in acetic acid are introduced into a round-bottomed flask. The stirring is maintained for 24 hours.

The medium is evaporated to dryness, the oily residue is triturated in anhydrous $Et_2O$, water is added and the solid formed is filtered. The medium is dried under vacuum over $P_2O_5$. 0.62 g (1.44 mmol) of a white solid is obtained.

Melting: >250° C.

The $^1H$ NMR is in agreement with the chemical structure.

Example 68

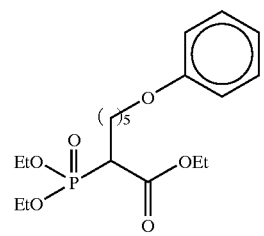

4.9 g (21.9 mmol) of triethylphosphonoacetate are dissolved in 21 ml of anhydrous DMF. The medium is cooled on ice to 0° C. and 0.56 g (21.9 mmol) of NaH is added in portions. The medium is stirred for 15 minutes at 0° C.

A solution of 5.33 g (21.9 mmol) of brominated derivative of Example 16 in 13 ml of anhydrous DMF is added. The medium is stirred overnight at room temperature.

The medium is diluted with $Et_2O$, washed with water, the organic phase is dried over $MgSO_4$, filtered and concentrated. 6.9 g of an oily residue are obtained, which residue is purified by chromatography on silica (eluent $Et_2O$).

5.33 g (63%) of oil are obtained.

Examples 69 to 71 are obtained according to the same procedure as that described for Example 68.

A solution of 5.33 g (13.8 mmol) of derivative of Example 68 in 32 ml of MeOH is stirred with 20.7 ml of M LiOH. The medium is heated for 1 hour under reflux.

The medium is evaporated to dryness, water is added and the medium is washed with $Et_2O$. The aqueous phase is acidified with an N HCl solution and it is extracted with $Et_2O$. The ethereal phases are combined, dried over $MgSO_4$, filtered and concentrated. 3.93 g (79%) of the desired acid are obtained.

Examples 73 to 75 are obtained according to the same procedure as that described for Example 72.

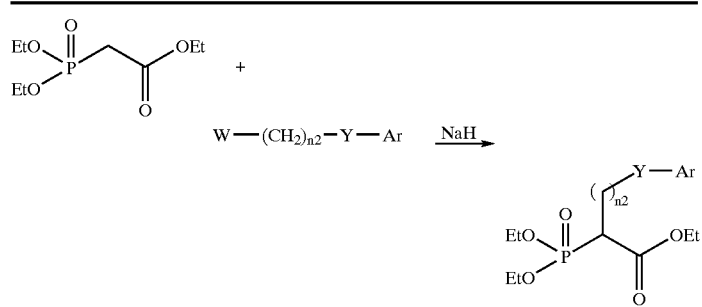

| Ex. No. | W—(CH$_2$)$_{n2}$—Y—Ar | product |
|---|---|---|
| 69 | ex 7 | 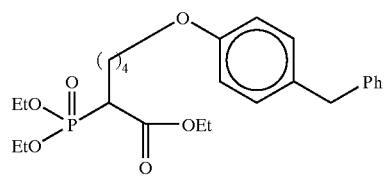 |
| 70 | ex 15 | 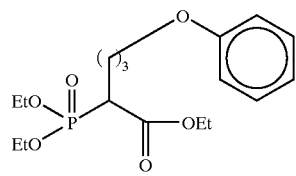 |
| 71 | ex 17 | 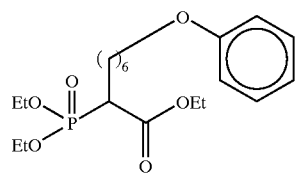 |

Example 72

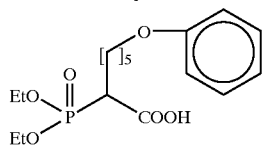

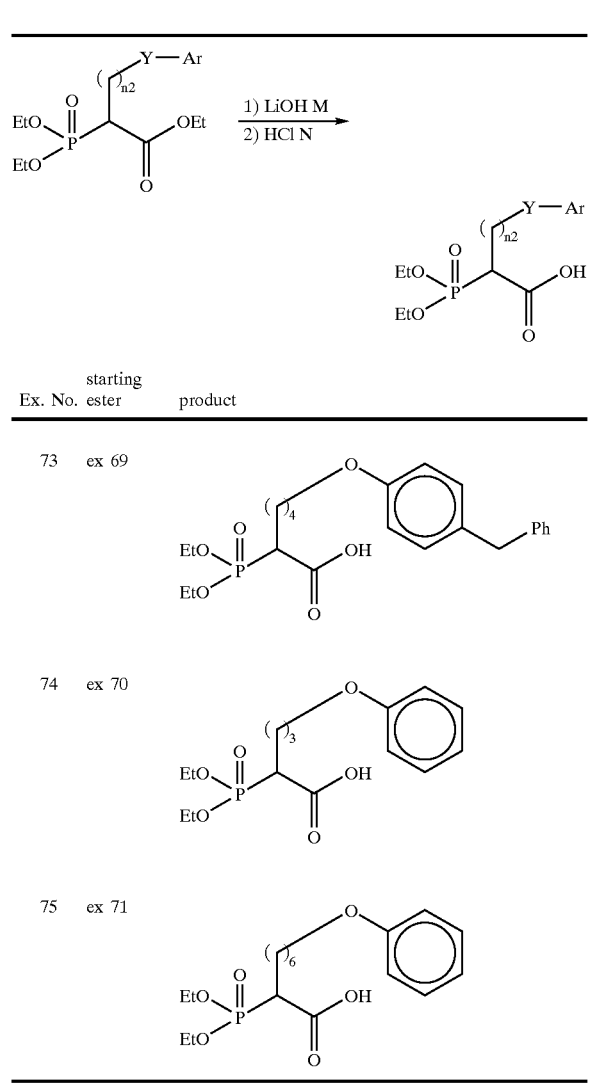

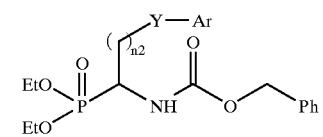

| Ex. No. | starting ester | product |
|---|---|---|
| 77 | ex 73 | 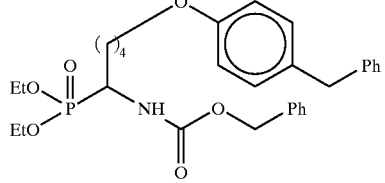 |
| 78 | ex 74 | 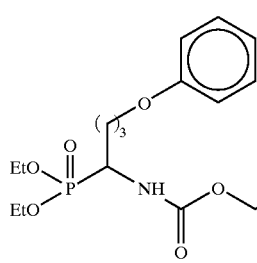 |
| 79 | ex 75 | 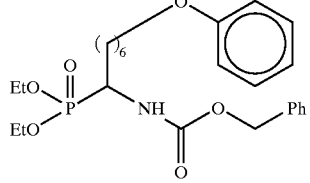 |

Example 80

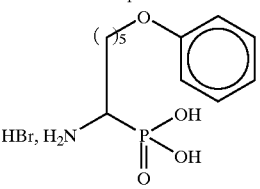

The acid of Example 72 is converted to carbamate 76 according to the same procedure as that described in Example 34.

Examples 77 to 79 are obtained according to the same procedure as that described in Example 34.

The phosphonate of Example 76 is converted to an aminophosphonic derivative according to the same procedure as that described in Example 67 (melting >250° C.)

The $^1$H NMR is in agreement with the chemical structure.

Examples 81 to 83 are obtained according to the same procedure as that described in Example 67.

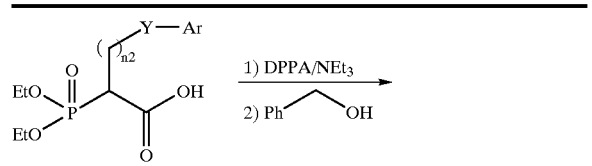

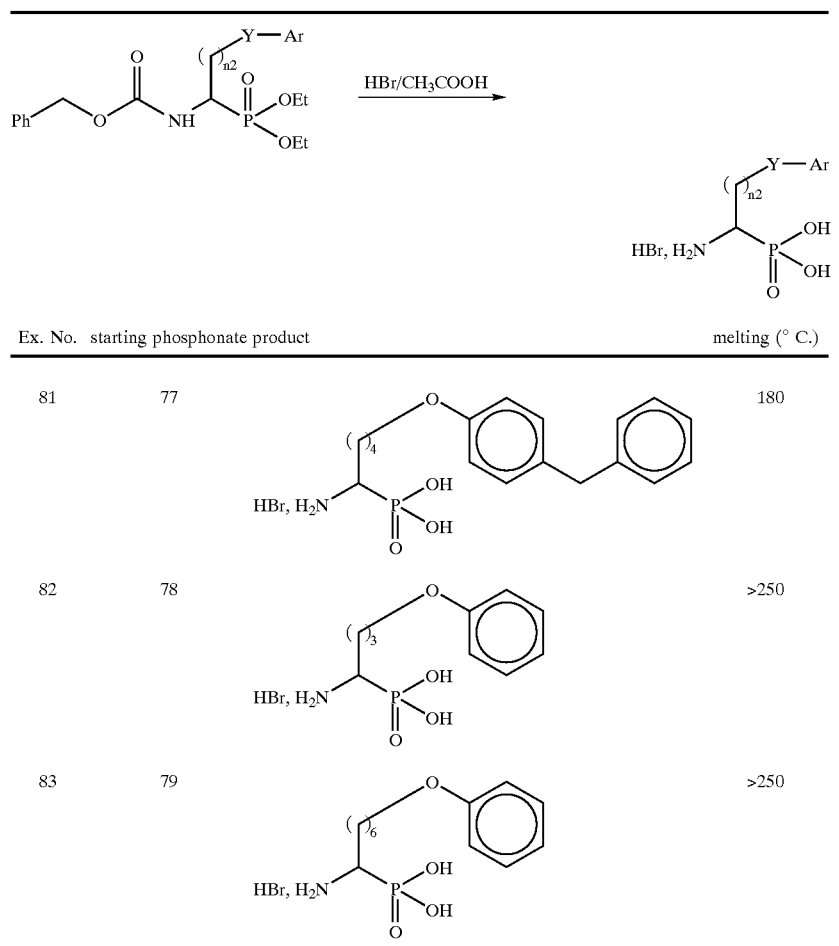

| Ex. No. | starting phosphonate | product | melting (° C.) |
|---|---|---|---|
| 81 | 77 | | 180 |
| 82 | 78 | | >250 |
| 83 | 79 | | >250 |

Example 84

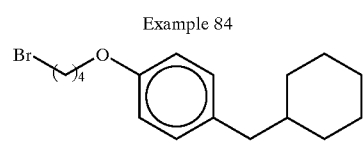

The compound of Example 84 is prepared from 1,4-dibromobutane and 4-(cyclohexylmethyl)phenol (Helv. Chem. Acta. Vol 77, (1994), 1241 and 1255) according to the same procedure as that described for Example 7 (method b).

Example 85

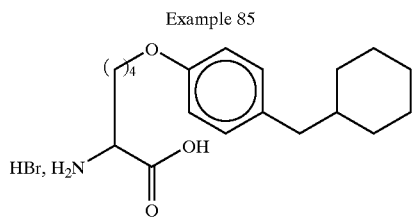

The product of Example 85 is prepared according to the same reaction sequence as that used for the synthesis of Example 51.

Melting: 121° C.

Example 86

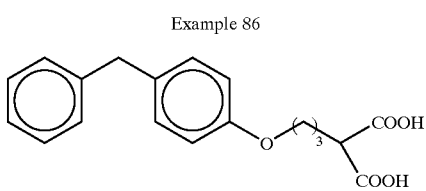

The diester of Example 19 is saponified according to the same procedure as that described in Example 59.

Example 87

The diacid of Example 86 is decarboxylated at 130° C. for 30 minutes.

A solution of 10.27 g (36.1 mmol) of the acid obtained after decarboxylation in 30 ml of anhydrous $Et_2O$ is added to a suspension of 1.64 g (1.2 equivalents) of $LiAlH_4$ in 47 ml of anhydrous $Et_2O$. The medium is stirred overnight at room temperature.

After hydrolysis and filtration, 7.68 g (28.4 mmol) of the desired alcohol are obtained.

Example 88

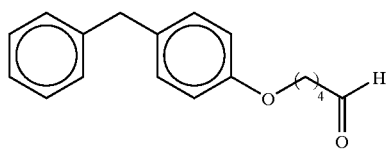

7.68 g (28.4 mmol) of the preceding alcohol dissolved in 35 ml of $CH_2Cl_2$ are added at 0° C. to 12.25 g (2 equivalents) of pyridinium chlorochromate dissolved in 56 ml of $CH_2Cl_2$. After 3 hours at room temperature, the medium is filtered on silica and purified by flash chromatography (eluent 7/3 heptane/$Et_2O$).

4.63 g (17.25 mmol) of aldehyde are obtained.

Example 89

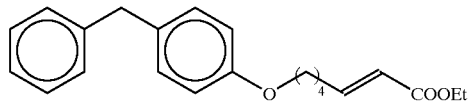

523 mg (1.2 equivalents) of NaH are added at 0° C. to a solution of 3.77 g (1.2 equivalents) of trimethylphosphonoacetate in 52 ml of anhydrous THF. The medium is stirred for 15 minutes at 0° C. and then a solution of 4.63 g (17.25 mmol) of aldehyde of Example 88 in 20 ml of anhydrous THF is added and the medium is stirred for 4 hours at room temperature.

The medium is evaporated, water is added, the medium is extracted with $Et_2O$, dried with $MgSO_4$ and then evaporated. The medium is purified by chromatography on silica (eluent 1/9 $Et_2O$/heptane).

2.56 g (7.89 mmol) of the desired ester are obtained.

Example 90

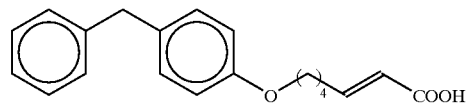

16 ml of N NaOH are added to 2.56 g (7.9 mmol) of the preceding ester dissolved in 26 ml of MeOR. The medium is heated for one hour under reflux, acidified with N HCl, extracted with $Et_2O$, dried over $MgSO_4$, filtered and concentrated.

2.36 g (7.6 mmol) of the desired acrylic acid are obtained.

Example 91

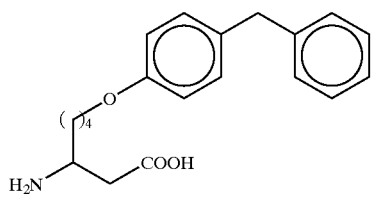

The preceding acid is treated according to the same procedure as that described in Example 61.

Melting: 205° C.

The $^1$H NMR is in agreement with the chemical structure.

Example 92

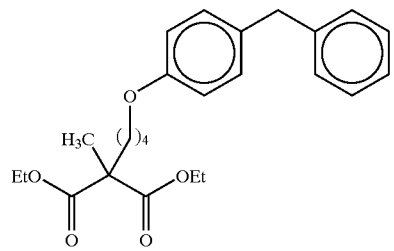

Diethyl methyl malonate is alkylated with the brominated derivative of Example 7 according to the same procedure as that described in Example 18.

Example 93

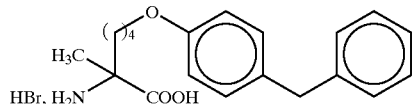

The product of Example 92 is treated according to the same reaction sequence as that used for the synthesis of Example 51.

Melting: 196° C.

Example 94

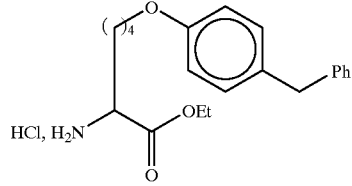

The carbamate of Example 38 is hydrogenated according to the same procedure as that described for Example 42 to lead to Example 94.

Melting >250° C.

Example 95

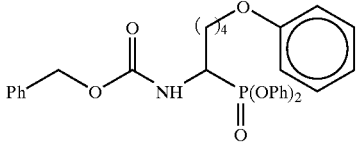

The same procedure is used as that described in Example 66 except that the diethyl phosphite is replaced with diphenyl phosphite.

Example 96

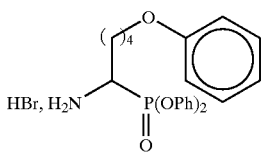

The product of the preceding example, 0.5 g (1 mmol), is stirred in 2 ml HBr/CH$_3$COOH at 30% for 2 hours.

The medium is evaporated to dryness and triturated in dry Et$_2$O until precipitation of the salt occurs.

0.4 g of the desired product is obtained after filtration and drying.

The $^1$H NMR is in agreement with the chemical structure.

Example 97

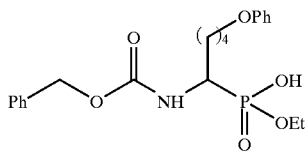

0.3 g of NBu$_4$Br and 8 ml of 2N NaOH are added to 1 g (2.22 mmol) of product of Example 66. The medium is stirred for 2 days at room temperature.

The medium is diluted with water and washed with Et$_2$O. The aqueous phase is acidified with N HCl and then concentrated H$_2$SO$_4$. The medium is extracted with Et$_2$O, dried over MgSO$_4$ and evaporated. 0.41 g of the desired product is obtained.

Example 98

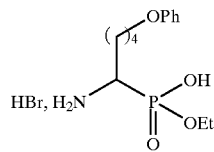

The product of Example 97 is deprotected according to the same procedure as that described in Example 96.

Example 99

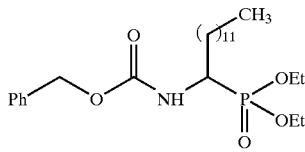

The same procedure is used as that described in Example 66 except that the aldehyde of Example 65 is replaced with tridecanal.

Example 100

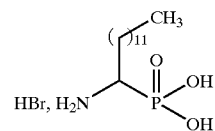

The product of Example 99 is deprotected according to the same procedure as that described in Example 67.

Melting: 252° C.

The $^1$H NMR is in agreement with the chemical structure.

Example 101

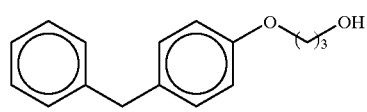

4.4 g (31.67 mmol) of 3-bromo-1-propanol, 4.9 g (26.5 mmol) of 4-hydroxydiphenylmethane, 11 g (79.59 mmol) of powdered K$_2$CO$_3$ and 45 ml of anhydrous DMF are successively introduced into an Erlenmeyer flask.

The medium is stirred overnight at room temperature.

The medium is filtered and the filtrate is taken up in 30 ml of ethyl acetate. The organic phase is washed with water (twice 10 ml) and then with a saturated aqueous NaCl solution (once 10 ml), dried over MgSO$_4$, filtered and concentrated.

The residue is purified by flash chromatography on silica with the ethyl ether/heptane (50/50) mixture. 5.35 g (22.07 mmol) of the expected product are obtained.

Example 102

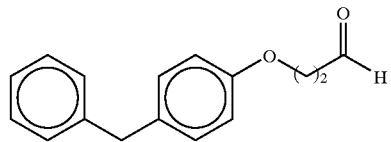

The alcohol of Example 101 is oxidized according to the same procedure as that described in Example 88.

Example 103

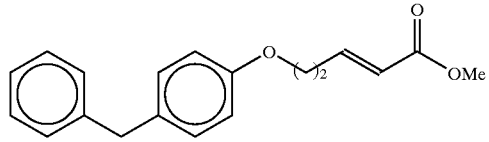

2.97 g (1.1 equivalents) of trimethylphosphonoacetate and 0.69 g (1.1 equivalents) of lithium hydroxide are successively added to a solution of 3.56 g (14.8 mmol) of aldehyde of Example 102 in 15 ml of anhydrous THF. The medium is stirred overnight at room temperature under argon. 100 ml of ethyl ether are added and the organic phase is washed with water (twice 10 ml) and with a saturated aqueous NaCl solution (once 10 ml).

The organic phase is dried over molecular sieve, filtered and concentrated. The medium is purified by chromatography on silica (eluent, Et$_2$O/heptane 1/9). 2.27 g (7.66 mmol) of the desired ester are obtained.

Example 104

The ester of Example 103 is saponified according to the same procedure as that described in Example 90.

Example 105

The preceding acid is treated according to the same procedure as that described in Example 61.

Melting: 240° C.

The $^1$H NMR is in agreement with the chemical structure.

Example 106

10 g (54.28 mmol) of 4-hydroxydiphenylmethane, 1.86 g (0.1 equivalent) of nBu$_4$NB$_r$, 7.2 g (1.5 equivalents) of ethylene carbonate and 100 ml of anhydrous DMF are successively added to a three-necked round-bottomed flask. The medium is heated at 140° C. under argon for 4 hours. It is allowed to return to room temperature, 100 ml of ethyl ether are added and the organic phase is washed with water (3 times 40 ml) and then with a saturated aqueous NaCl solution (once 20 ml). The organic phase is dried over molecular sieve, filtered and concentrated. The residue is purified by flash chromatography on silica with an ethyl ether/heptane (50/50) mixture.

6.4 g of the expected product are obtained.

Example 107

2.14 g (1.2 equivalents) of SOCl$_2$ and then 76 mg (1.1 mmol) of imidazole are added, at a temperature of about +5° C., to 3.41 g (15 mmol) of alcohol of Example 106. The medium is stirred for 15 minutes at room temperature and then for 4 hours at 100° C. The medium is then allowed to return to room temperature, 20 ml of water are added and the aqueous phase is neutralized with NaHCO$_3$ and extracted with ethyl ether (twice 20 ml). The organic phase is dried over molecular sieve, filtered and concentrated. 3.45 g (13.98 mmol) of the expected chlorinated derivative are obtained.

Example 108

The diester of Example 108 is prepared according to the same procedure as that described in Example 18, but starting with the chlorinated derivative 107.

Example 109

The diester of Example 108 is saponified according to the same procedure as that described in Example 59.

Example 110

The diacid of Example 109 is decarboxylated and reduced according to the same procedure as that described in Example 87.

Example 111

The alcohol of Example 110 is oxidized according to the same procedure as that described in Example 88.

Example 112

The aldehyde of Example 111 is converted to the ester 112 by a Wittig Horner reaction according to the same procedure as that described in Example 103.

Example 113

The ester of Example 112 is saponified according to the same procedure as that described in Example 90.

Example 114

The acid 113 is treated according to the same procedure as that described in Example 61.

Melting: 226° C.

The $^1$H NMR is in agreement with the chemical structure.

Biological Activity

Biological Trials of the Compounds According to the Invention

1) Inhibition of the Aminopeptidase Activity of Recombinant LTA$_4$ Hydrolase

The compounds were tested using human recombinant LTA$_4$ hydrolase (Minami et al., FEBS Letters, 1988, 229: 279). The LTA$_4$ hydrolase expressed by *E. coli* JM109 is purified mainly according to Minami et al., (J. Biol. Chem., 1987, 262: 13873).

The inhibition of the aminopeptidase activity of the enzyme is measured by means of a fluorimetric method in 96-well microplates. The recombinant enzyme (0.5 µg in 50 µl of 50 mM Tris-HCl pH 7.4) is preincubated for 10 minutes at 37° C. in the presence of inhibitor and of dithiothreitol (DTT, 10$^{-5}$ M). The substrate alanyl-amido-methylcoumarin (Ala-AMC, 25 µM-Tris HCl 50 mM, pH 7.4) is added and the incubation is continued for 15 minutes at 37° C. The release of AMC is measured by fluorimetry.

To evaluate the specificity of the compounds according to the invention, some of them were also tested for their capacity to inhibit the activity of membrane aminopeptidase M (EC 3.4.11.2). The same test is carried out with 0.1 µg of aminopeptidase M (Pierce, USA).

2) Inhibition of the Biosynthesis of LTB$_4$ In Vitro

The biosynthesis of LTB$_4$ is measured in human whole blood in the presence of inhibitors of LTA$_4$ hydrolase according to the invention. A 50 µl blood sample collected over sodium heparinate is preincubated for 10 minutes at 37° C. in the presence of inhibitor (50 mM Tris-HCl, 0.15 M NaCl, 10$^{-5}$ M DTT, pH 7.4).

The LTA$_4$ substrate was freshly prepared by alkaline hydrolysis of LTA$_4$ methyl ester (Cayman Chemical Co., USA). After incubating for 10 minutes in the presence of LTA$_4$ (1 µM in 50 mM Tris-HCl, 0.15 M NaCl, 0.5% BSA, pH 7.4), the reaction is stopped by diluting 1/20 in 0.1 M potassium phosphate buffer containing 1.5 mM NaN$_2$, 0.4 M NaCl, 1 mM EDTA, 0.1% BSA, pH 7.4, −4° C.

The LTB$_4$ is assayed by enzyme-linked immunoassay (Cayman Chemical Co., USA).

3) Inhibition of the Biosynthesis of LTB$_4$ Ex Vivo

The compounds inhibiting LTA$_4$ hydrolase according to the invention are suspended in 1.25% methyl cellulose and administered to mice by the oral route at the dose of 10 mg/kg. Thirty minutes later, the mice are sacrificed and the blood collected over lithium heparinate. The blood is then, as above, incubated for 10 minutes at 37° C. in the presence of LTA$_4$ and then the LTB$_4$ formed is assayed by enzyme-linked immunoassay.

The compounds of the invention have proved active in low concentration in vitro (for example the Ki of compound 51 was 32 nM) and in low dose by the oral route (<1 mg/kg, or even <0.1 mg/kg).

The compounds according to the invention, in particular those corresponding to one of the formulae (II) and (VI) allow the inhibition of LTA$_4$ hydrolase in vitro and in vivo. They also make it possible to inhibit the biosynthesis of LTB$_4$, which makes them compounds of interest in human therapy.

The compounds according to the invention may be administered in particular by the oral route.

They exhibit good bioavailability and low toxicity.

The compounds according to the invention, in particular the compounds of the aminophosphonate type, possess a long duration of action.

Accordingly, these compounds exert, over a period of more than 24 hours, complete inhibition of the blood LTA$_4$ hydrolase activity after administration by the oral route at doses of 1 to 1.0 mg/kg in rats.

What is claimed is:

1. A compound corresponding to the following formula (I):

wherein n$_1$ and n$_3$ are equal to 0 or 1, with (n$_1$+n$_3$) equal to 0 or 1 n$_2$ varies from 0 to 10 n$_4$ varies from 0 to 4

A$^1$ is selected from the following groups:
 a) cycloalkyl
 b) phenyl which is unsubstituted or which is mono- or polysubstituted with substituents selected from halogen atoms and CF$_3$, lower alkyl and lower alkoxy groups,
 c) 2-, 3-or 4-pyridyl
 d) 2- or 3-thienyl
 e) 2- or 3-furyl
 f) 2-, 3- or 4-piperidyl
 g) cycloalkenyl A$_2$ is selected from the following groups:
 a) cycloalkylene
 b) phenylene which is unsubstituted or which is mono- or polysubstituted with substituents from halogen atoms, CF$_3$, lower alkyl and lower alkoxy groups,

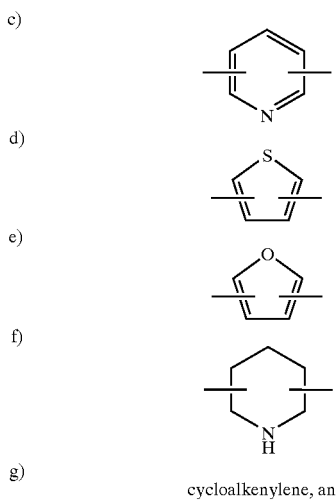

cycloalkenylene, and $R^2$ and $R^3$ are independently selected from the following groups:
i) a hydrogen atom
ii) a lower alkyl group
iii) a lower alkyl group substituted with a halogen atom
iv) a $CF_3$ group
v) a halogen atom.

2. The compound as claimed in claim 1, wherein $R^2$ and/or $R^3$ represents a hydrogen atom.

3. The compound as claimed in claim 2, wherein $R^2$ and $R^3$ represent a hydrogen atom.

4. The compound as claimed in claim 1, wherein $R^2$ and/or $R^3$ is different from hydrogen.

5. The compound as claimed in claim 1, wherein $n_1$ and $n_3$ are equal to 0.

6. The compound as claimed in claim 1, wherein $n_1$ or $n_3$ is different from 0.

7. The compound as claimed in claim 1 wherein $n_1$ equals 0, and $R_3$ equals H and $R^2$ equals H.

8. The compound as claimed in claim 1, wherein $n_2$ varies from 2 to 5.

9. The compound as claimed in claim 8, wherein $n_2$ is equal to 3.

10. The compound as claimed in claim 1, wherein $A^2$ represents a phenylene group.

11. The compound as claimed in claim 1, wherein $n_4$ is equal to 0 or 1.

12. The compound as claimed in claim 1, wherein $A^1$ is a phenyl, cycloalkyl or cycloalkenyl.

13. The compound as claimed in claim 1, wherein $A^1$ is a phenyl group.

14. The compound as claimed in claim 1, wherein they are selected from:

1) (S)-O-4-benzylphenylserine hydrochloride
2) 2-(RS)-amino-6-(4-benzylphenoxy)hexanoic acid hydrobromide
3) 2-(RS)-amino-5-(4-benzylphenoxy)pentanoic acid hydrobromide
5) 2-(RS)-amino-7-(4-benzylphenoxy)heptanoic acid hydrobromide
6) 2-(RS)-amino-6-(4-phenylphenoxy)hexanoic acid hydrobromide
8) 2-(RS)-amino-8-(4-benzylphenoxy)octanoic acid hydrobromide
10) 2-(RS)-aminomethyl-6-(4-benzylphenoxy)hexanoic acid
16) 2-(RS)-amino-6-(4-cyclohexylmethylphenoxy)hexanoic acid hydrobromide
17) 3-(RS)-amino-7-(4-benzylphenoxy)heptanoic acid
18) 2-(RS)-amino-2-methyl-6-(4-benzylphenoxy)hexanoic acid hydrobromide
20) 3-(RS)-amino-5-(4-benzylphenoxy)pentanoic acid
21) 3-(RS)-amino-6-(4-benzylphenoxy)hexanoic acid.

15. A pharmaceutical composition comprising a compound of formula (I) according to claim 1 with a pharmaceutically acceptable excipient.

16. A method for inhibiting $LTA_4$ hydrolase comprising administering the compound of formula (I) as claimed in claim 1 to a mammal.

17. A method for treating inflammation comprising administering the compound of formula (I) as claimed in claim 1 to a mammal, wherein said inflammation involves $LTA_4$ hydrolase.

18. An antiarthritic treatment method comprising administering the compound of formula (I) as claimed in claim 1 to a mammal.

19. An antipsoriatic treatment method comprising administering the compound of formula (I) as claimed in claim 1 to a mammal.

20. A hepatoprotective treatment method comprising administering the compound of formula (I) as claimed in claim 1 to a mammal in need of such hepatoprotective treatment.

21. An antimitotic treatment method comprising administering the compound of formula (I) as claimed in claim 1 to a mammal.

22. A method for treating an overproduction of $LTB_4$, induced in particular by cyclooxygenase inhibitors, comprising administering the compound of formula (I) as claimed in claim 1 to a mammal.

23. A process for inhibiting the activity of $LTA_4$ hydrolase comprising administering to a mammal in need of said inhibition the compound as claimed in claim 1 of formula (I) where $n_1=n_3=0$, $R^2=H$ and $n_2=1$.

24. A process for treating inflammation comprising administering 10 a mammal in need of said treatment the compound as claimed in claim 1 of formula (I) where $n_1=n_3=0$, $R^2=H$ and $n_2=1$, wherein said inflammation involves $LTA_4$ hydrolase.

25. A process for treating arthritis comprising administering to a mammal in need of said treatment the compound as claimed in claim 1 of formula (I) where $n_1=n_3=0$, $R^2=H$ and $n_2=1$.

26. A process for treating psoriasis comprising administering to a mammal in need of said treatment the compound as claimed in claim 1, of formula (I) where $n_1=n_3=0$, $R^2=H$ and $n_2=1$.

27. A process for hepatoprotective treatment comprising administering to a mammal in need of said treatment the compound as claimed in claim 1, of formula (I) where $n_1=n_3=0$, $R^2=H$ and $n_2=1$.

28. A process for an antimitotic treatment comprising administering to a mammal in need of said treatment the compound as claimed in claim 1 of formula (I) where $n_1=n_3=0$, $R^2=H$ and $n_2=1$.

29. A process for the treatment of an overproduction of $LTB_4$ induced in particular by a cyclooxygenase inhibitor comprising administering to a mammal in need of said treatment the compound as claimed in claim 1 of formula (I) where $n_1=n_3=0$, $R^2=H$ and $n_2=1$.

30. A pharmaceutical composition, comprising as an active ingredient the compound of formula (I) as claimed in claim 1 and a cyclo-oxgenase inhibitor selected from the group consisting of aspirin, ibuprofen and diclofenac.

* * * * *

UNITED STATES PATENT AND TRADEMARK OFFICE
CERTIFICATE OF CORRECTION

PATENT NO. : 6,878,723 B1
DATED : April 12, 2005
INVENTOR(S) : Danvy

It is certified that error appears in the above-identified patent and that said Letters Patent is hereby corrected as shown below:

<u>Column 58,</u>
Line 50, after "$n_4$ varies from 0 to 4" insert -- Y is –O– --.

<u>Column 59,</u>
Line 28, after "v) a halogen atom" insert -- as well as their isomers, diastereoisomers and enantiomers and their therapeutically acceptable salts --.

Signed and Sealed this

Thirtieth Day of May, 2006

JON W. DUDAS
*Director of the United States Patent and Trademark Office*